United States Patent
Tedesco et al.

(10) Patent No.: US 8,824,784 B2
(45) Date of Patent: *Sep. 2, 2014

(54) SYSTEM FOR IMAGE ANALYSIS IN A NETWORK THAT IS STRUCTURED WITH MULTIPLE LAYERS AND DIFFERENTIALLY WEIGHTED NEURONS

(71) Applicant: Facebook, Inc., Menlo Park, CA (US)

(72) Inventors: Daniel E. Tedesco, Huntington, CT (US); James A. Jorasch, Stamford, CT (US); Geoffrey M. Gelman, Stamford, CT (US); Jay S. Walker, Ridgefield, CT (US); Stephen C. Tulley, Fairfield, CT (US); Vincent M. O'Neil, New York, NY (US); Dean P. Alderucci, Westport, CT (US)

(73) Assignee: Facebook, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/731,824

(22) Filed: Dec. 31, 2012

(65) Prior Publication Data

US 2013/0144976 A1    Jun. 6, 2013

Related U.S. Application Data

(63) Continuation of application No. 13/291,889, filed on Nov. 8, 2011, now Pat. No. 8,345,963, which is a continuation of application No. 11/427,489, filed on Jun. 29, 2006, now Pat. No. 8,081,817, which is a (Continued)

(51) Int. Cl.
*G06K 9/00* (2006.01)
*G08B 13/196* (2006.01)
*H04L 29/08* (2006.01)
*G06F 17/30* (2006.01)
*H04L 29/06* (2006.01)

(52) U.S. Cl.
CPC .......... *H04L 67/12* (2013.01); *G08B 13/19673* (2013.01); *G08B 13/1968* (2013.01); *G06F 17/30256* (2013.01); *G08B 13/19641* (2013.01); *H04L 63/08* (2013.01); *G08B 13/19656* (2013.01); *G06F 17/30259* (2013.01); *G08B 13/19663* (2013.01)
USPC .......... 382/159; 382/103; 382/156; 709/203; 709/219

(58) Field of Classification Search
USPC .............. 340/506; 379/45, 49; 382/103, 156, 382/159; 725/105
See application file for complete search history.

(56) References Cited

U.S. PATENT DOCUMENTS 7,069,310 B1 * 6/2006 Bartholomew ................ 709/219
7,227,569 B2 * 6/2007 Maruya ........................ 348/143

(Continued)

*Primary Examiner* — Gregory M Desire
(74) *Attorney, Agent, or Firm* — Baker Botts L.L.P.

(57) ABSTRACT

Disclosed herein are systems and methods for facilitating the usage of an online workforce to remotely monitor security-sensitive sites and report potential security breaches. In some embodiments, cameras are configured to monitor critical civilian infrastructure, such as water supplies and nuclear reactors. The cameras are operatively connected to a central computer or series of computers, and images captured by the cameras are transmitted to the central computer. After initially registering with the central computer, Guardians "log on" to a central website hosted by the central computer and monitor the images, thereby earning compensation. Site owners compensate the operator of the computer system for this monitoring service, and the operator in turn compensates Guardians based on, for example, (i) the amount of time spent monitoring, and/or (ii) the degree of a given Guardian's responsiveness to real or fabricated security breaches.

20 Claims, 2 Drawing Sheets

Related U.S. Application Data continuation of application No. 10/786,831, filed on Feb. 25, 2004, now Pat. No. 7,292,723.

(60) Provisional application No. 60/450,465, filed on Feb. 26, 2003, provisional application No. 60/450,459, filed on Feb. 26, 2003, provisional application No. 60/466,497, filed on Apr. 29, 2003, provisional application No. 60/491,574, filed on Jul. 31, 2003.

(56) References Cited

U.S. PATENT DOCUMENTS

| | | | | |
|---|---|---|---|---|
| 7,281,054 | B2 * | 10/2007 | Ishioka et al. | 709/231 |
| 8,462,994 | B2 * | 6/2013 | Ortiz et al. | 382/115 |
| 2002/0198780 | A1 * | 12/2002 | Kawakami et al. | 705/14 |

* cited by examiner

SYSTEM FOR IMAGE ANALYSIS IN A NETWORK THAT IS STRUCTURED WITH MULTIPLE LAYERS AND DIFFERENTIALLY WEIGHTED NEURONS

RELATED APPLICATIONS

This nonprovisional application is a continuation of and claims the benefit of priority of U.S. patent application Ser. No. 13/291,889, filed 8 Nov. 2011, and entitled "SYSTEM FOR IMAGE ANALYSIS IN A NETWORK THAT IS STRUCTURED WITH MULTIPLE LAYERS AND DIFFERENTIALLY WEIGHTED NEURONS," which is a continuation of and claims the benefit of priority of U.S. patent application Ser. No. 11/427,489, filed 29 Jun. 2006, issued as U.S. Pat. No. 8,081,817, and entitled "SYSTEM FOR IMAGE ANALYSIS IN A NETWORK THAT IS STRUCTURED WITH MULTIPLE LAYERS AND DIFFERENTIALLY WEIGHTED NEURONS," which is a continuation of and claims the benefit of priority of U.S. patent application Ser. No. 10/786,831, filed 25 Feb. 2004, issued as U.S. Pat. No. 7,292,723, and entitled "SYSTEM FOR IMAGE ANALYSIS IN A NETWORK THAT IS STRUCTURED WITH MULTIPLE LAYERS AND DIFFERENTIALLY WEIGHTED NEURONS".

The present utility application claims the benefit of priority of the following U.S. Provisional Patent Applications:

Application No. 60/450,465, filed 26 Feb. 2003, entitled "SYSTEM AND METHOD FOR THE REMOTE MONITORING OF CRITICAL CIVILIAN INFRASTRUCTURE";

Application No. 60/450,459, filed 26 Feb. 2003, entitled "SYSTEM AND METHOD FOR THE REMOTE MONITORING OF CRITICAL CIVILIAN INFRASTRUCTURE";

Application No. 60/466,497, filed 29 Apr. 2003, entitled "SYSTEM AND METHOD FOR THE PERFORMANCE AND COMPENSATION OF MICRO-TASKS"; and Application No. 60/491,574, filed 31 Jul. 2003, entitled "SYSTEM AND METHOD FOR THE REMOTE MONITORING OF PRIVATE PROPERTY".

BACKGROUND

Many forms of violence and intimidation are of great concern to various entities, ranging from individuals to nations. The United States and other developed nations face an unprecedented challenge posed by terrorism, both foreign and domestic.

The unprecedented magnitude of the threat is even worse than generally believed, and can only be appreciated by considering the quantity and value of other potential targets, e.g., on the U.S. homeland. In addition to the well understood targets such as airport terminals and large commercial centers, there are tens of thousands of critical infrastructure facilities in the U.S., including airport perimeters, chemical plants, natural gas plants, pipelines and pumping stations, nuclear and non-nuclear power plants, refineries and reservoirs.

Such facilities which are typically unguarded. Many people could, with relative ease, approach within one hundred feet of such facilities.

Thus, given the magnitude of the problem posed by modern terrorism there exists a clear and urgent need for systems and methods that to combat terrorism.

Novel image processing techniques may be employed in various applications to help combat terrorism.

DESCRIPTION OF EXAMPLE EMBODIMENT(S)

The embodiments described in this application are presented for illustrative purposes only and are not meant to be limiting in any sense. The invention is widely applicable to numerous embodiments, as is readily apparent from the disclosure herein.

The terms "an embodiment", "embodiment", "embodiments", "the embodiment", "the embodiments" "one or more embodiments", "some embodiments", and "one embodiment" mean "one or more embodiments" unless expressly specified otherwise.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order.

It will be readily apparent that the various methods and algorithms described herein may be implemented by, e.g., appropriately programmed general purpose computers and computing devices. Further, programs which implement such methods and algorithms may be stored and transmitted in a variety of known media.

Among the many uses of the disclosed systems and methods, Applicants have realized that there are a significant number of vulnerable sites which may be subject to hostile acts. Applicants have also realized that such sites are typically unguarded and lack access control, and further that such access control would typically be cost prohibitive. Applications have also realized that typically people are not permitted to be at or near such sites. Applicants have also realized that very many people may be used, but are not currently being used, to perform various types of productive work, especially from their homes or other convenient locations.

While the methods and apparatus of the present invention are described herein by way of particular embodiments, those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

Figure 1:
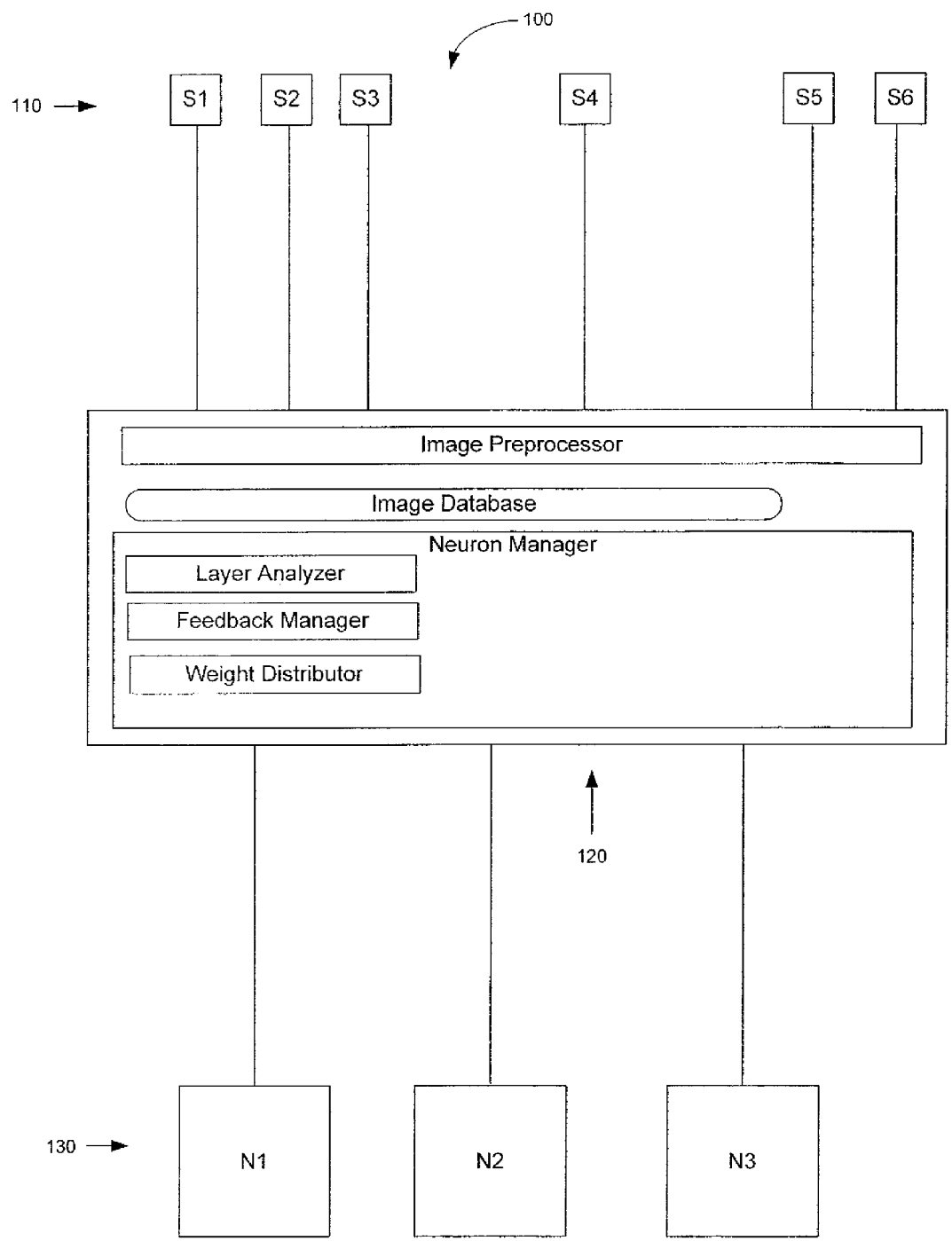
FIG. 1 is an illustration of a network according to one embodiment of the invention.

FIG. 1 is an illustration of a network 100 according to one embodiment of the invention. In FIG. 1, a plurality of sensors 110, such as image capture devices, communicate (unidirectionally or bidirectionally) with an image processing and distribution node 120, which may also be referred to herein as a "central computer" or "central server". The image processing and distribution node 120 may also be capable of transmitting signals to sensors, either by individually addressing certain sensor(s) or by broadcasting to some or all sensors.

In some embodiments, if the sensor is an image capture device such as a camera, images posted from cameras may be optimized for processing/review according to image processing rules. Such rules may function to, for example, grayscale the image, enhance brightness and/or sharpness, and/or magnify or highlight certain portions of the image. The pre-processing software can be configured at the site level to tune it to the visual characteristics of a particular site (e.g., heavy sun glare at certain hours). The "raw" (pre-processing) image may be retained for a site-defined time period before getting discarded.

In an embodiment where the sensors are image capture devices, image capture devices may employ on-board motion detection capabilities to trigger image capture events. Also, image capture devices may forward captured images to the image processing and distribution node. The image processing and distribution node may preprocess the received images, and then store the (preprocessed) images. The database may create an association with the images. For example, images can be keyed in the database to the location of the images.

In some embodiments, processed images may be given a unique index number that associates them with the source site/node. Processed images may be given a digital watermark and/or a digital fingerprint may be taken of the image (e.g., via an MD5 checksum) to facilitate authentication of the image in its final form.

Sensed data (e.g., images) is processed by a plurality of neurons 130 according to a processing algorithm. Each neuron processes at least one received file corresponding to sensed data, and in turn generates a result based on the processing.

Figure 2:
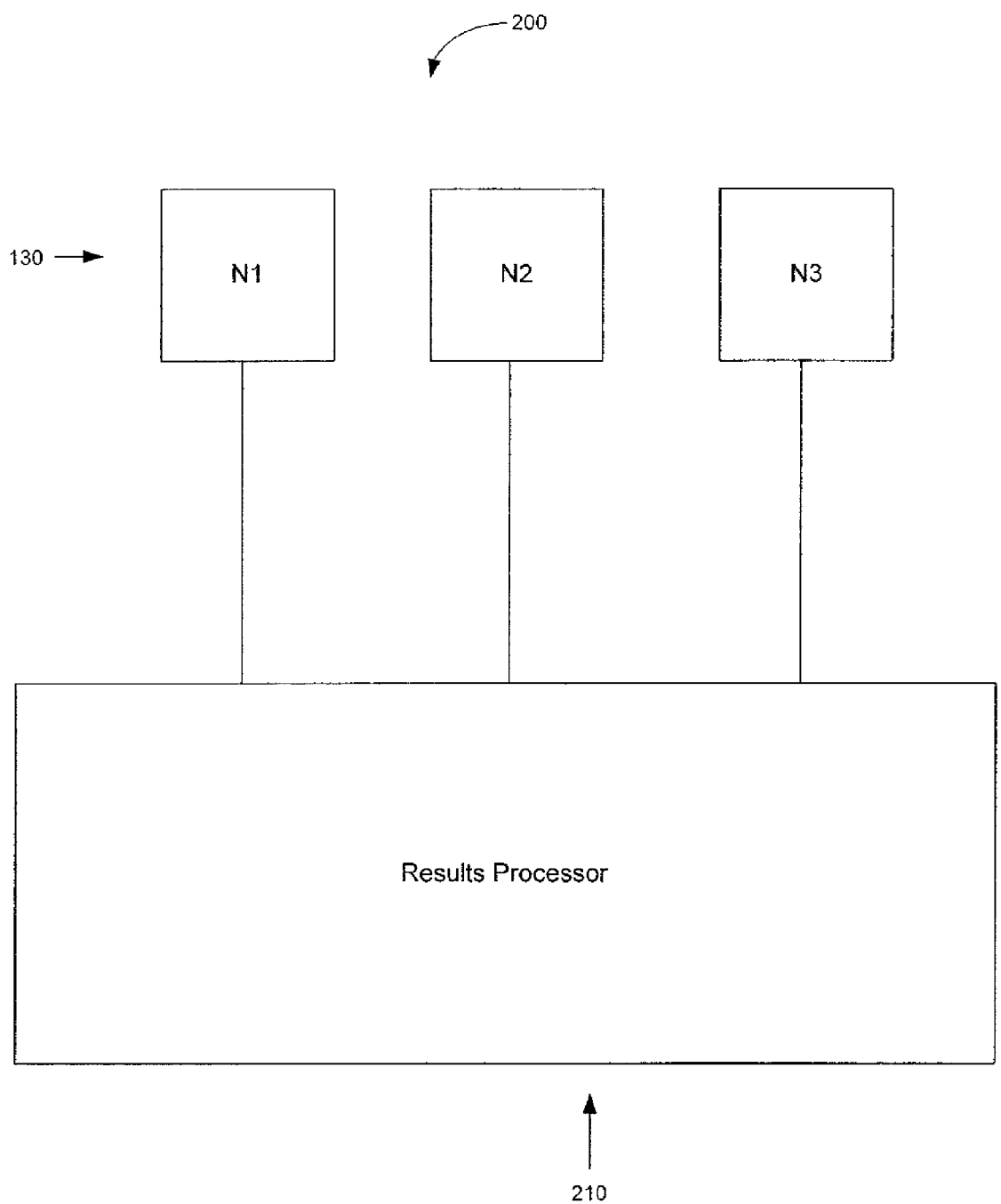
FIG. 2 is an illustration of a network according to one embodiment of the invention.

Referring to FIG. 2, in another perspective of a network 200, neurons 130 transmit results to a results processor 210, which may be the image processing and distribution node or may be a separate device.

Each neuron has at least one respective weight that is used to evaluate the processed results from that neuron. Results from neurons with lower weights may be distrusted. A weight distributor assigns weights to neurons, and updates those weights as appropriate. For example, a neuron which has generated faulty results may be assigned reduced weight. Similarly, a neuron which has generated accurate results may be assigned a higher weight.

Also, a neuron may have more than one weight. For example, a neuron may have a different weight to represent the neuron's "accuracy" in evaluating different types of sensed data (e.g., different weights for different types of images, different weights for images vs. audio data).

Neurons are typically configured to generate extremely simple results, leading to efficient processing of results. In one embodiment, a neuron is only responsible for generating a binary result from a sensed data file. For example, a neuron may be responsible for generating a bit to represent whether or not a received image depicts a human (e.g., 1=human present in the image, 0=no human present in the image).

Neurons may be arranged in "layers" to provide enhanced accuracy and reliability. For example, neurons in a first layer may each have a higher weight than neurons in a second layer. In such an embodiment, neurons in the first layer may be more accurate and/or more trusted, and accordingly a neuron in the first layer could supervise one or more neurons in the second layer. It is also possible that neurons transition among layers as their weights are adjusted by the weight distributor. A layer analyzer can be used to allocate neurons to different layers, based on their weights and other criteria. The layer analyzer can also segment a layer so that different portions of a layer are used for different types of processing (e.g., different types of images, different types of sensed data)

A feedback manager can be configured to process results from neurons. The feedback manager may direct neurons to perform additional processing based on the results. For example, if a neuron processes particular sensed data (e.g., an image) to provide a "positive result" and/or a result which is believed to be atypical (e.g., human present in the image when no human should be), then the feedback manager may, for example, (i) direct the sensed data to be processed by additional neurons, e.g., in order to verify the result; (ii)

Sensed data which is processed by a neuron with a relatively low weight may be directed to other neurons for redundant or additional processing. Similarly, the number of additional neurons to which sensed data is directed may be based on the weight of the original or first neuron.

Exemplary Network Configuration

The present invention can be configured to work in a network environment whereby the central computer, the user computer and/or the monitoring device communicate with each other directly or indirectly, via a wired or wireless medium such as the Internet, LAN, WAN or Ethernet, Token Ring, or via any appropriate communications means or combination of communications means. Communication between the devices and computers, and among the devices, may be direct or indirect, such as over the Internet through a Website maintained by a computer on a remote server or over an on-line data network including commercial on-line service providers, bulletin board systems and the like. In yet other embodiments, the devices may communicate with one another and/or a computer over RF, cable TV, satellite links and the like.

Some, but not all, possible communication networks that may comprise the network or be otherwise part of the system include: a local area network (LAN), a wide area network (WAN), the Internet, a telephone line, a cable line, a radio channel, an optical communications line, and a satellite communications link. Possible communications protocols that may be part of the system include: Ethernet (or IEEE 802.3), SAP, ATP, Bluetooth™, and TCP/IP. Further, networking of devices and computers may include use of 802.11b and related wireless protocols and/or use of cell networks (GSM and other emerging standards).

Those skilled in the art will understand that computers and devices in communication with each other need not be continually transmitting to each other. On the contrary, such computers and devices need only transmit to each other as necessary, and may actually refrain from exchanging data most of the time. For example, a device in communication with another device via the Internet may not transmit data to the other device for weeks at a time.

In an embodiment, a central computer may not be necessary and/or preferred. For example, the present invention may, in one or more embodiments, be practiced on a monitoring device in communication only with one or more user computers. In such an embodiment, any functions described as performed by the central computer or data described as stored on the central computer may instead be performed by or stored on one or more monitoring devices or user computers.

Network Security

Communication among computers and devices may be encrypted to ensure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc., 2d ed., 1996.

Data Storage Devices/Memory

For each computer and/or device (i.e., the central computer, the user computer, and/or the monitoring apparatus), a processor may be in communication with a memory and a communications port (e.g., for communicating with one or more other computers or devices). The memory may comprise an appropriate combination of magnetic, optical and/or semiconductor memory, and may include, for example, Random Access Memory (RAM), Read-Only Memory (ROM), a compact disc and/or a hard disk. The memory may comprise or include any type of computer-readable medium. The processor and the memory may each be, for example: (i) located entirely within a single computer or other device; or (ii) connected to each other by a remote communication medium, such as a serial port cable, telephone line or radio frequency transceiver.

In one, several or all computers or devices, a memory may store a program for controlling a processor. The processor performs instructions of the program, and thereby operates in accordance with the present invention, and particularly in accordance with the methods described in detail herein. The program may be stored in a compressed, uncompiled and/or encrypted format. The program furthermore includes program elements that may be necessary, such as an operating system, a database management system and "device drivers" for allowing the processor to interface with computer peripheral devices. Appropriate program elements are known to those skilled in the art, and need not be described in detail herein.

The term "computer-readable medium" as used herein refers to any medium that participates in providing instructions to a processor for execution. Such a medium may take many forms, including but not limited to, non-volatile media, volatile media, and transmission media. Non-volatile media include, for example, optical or magnetic disks, such as memory. Volatile media include dynamic random access memory (DRAM), which typically constitutes the main memory. Transmission media include coaxial cables, copper wire and fiber optics, including the wires that comprise a system bus coupled to the processor. Transmission media may carry acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying one or more sequences of one or more instructions to a processor for execution. For example, the instructions may initially be borne on a magnetic disk of a remote computer. The remote computer can load the instructions into its dynamic memory and send the instructions over a telephone line using a modem. A modem local to a particular computer or device can receive the data on the telephone line and use an infrared transmitter to convert the data to an infrared signal. An infrared detector can receive the data carried in the infrared signal and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of carrier waves that carry data streams representing various types of information. Thus, a computer or device may obtain instructions in the form of a carrier wave.

According to an embodiment of the present invention, the instructions of the program may be read into a main memory from another computer-readable medium, such from a ROM. The execution of sequences of the instructions in a program causes the processor perform the process steps described herein. In alternate embodiments, hard-wired circuitry may be used in place of, or in combination with, software instructions for implementation of the processes of the present invention. Thus, embodiments of the present invention are not limited to any specific combination of hardware and software.

The memory also stores a plurality of databases, including (1) a site database, and (2) a Guardian database. Some or all of the data stored in each database is described in conjunction with the following description of the process steps. The described entries of the databases represent exemplary information only; those skilled in the art will understand that the number and content of the entries can be different from those illustrated herein. Further, despite any description of the databases as tabular, relational databases, an object-based model could be used to store and manipulate the data types of the present invention and likewise, object methods or behaviors can be used to implement the processes of the present invention.

Site Registration

Site owners and/or operators such as owners of nuclear facilities, chemical plants, and airports must initially register with the system in order have their sites monitored by Guardians. It is contemplated that site owners will purchase camera and/or other monitoring device equipment from the operator of the central computer, although it is possible that site owners may register other existing cameras and/or other monitoring devices with the central computer. In some embodiments, the cameras distributed to site owners are mounted atop poles that can be easily erected in the ground.

In embodiments where monitoring devices comprise cameras such as video cameras, cameras and supporting peripheral hardware may have embedded computer devices and may support various standard internetworking and operating system protocols (e.g., embedded Linux chips that support HTTP, SSL, FTP, CGI, Java, etc.). For example, cameras available from Axis®. Communications, Inc. may be employed, including model 2420 series network cameras with infrared (IR) lenses, model 250-S MPEG-2 network video servers, and model 2191 audio modules. Infrared lenses may be desirable for low-light (i.e., nighttime) image capture.

In some embodiments, cameras may also be equipped with PTZ (Pan/Tilt/Zoom) mechanisms to facilitate remote adjustment of field of view, focus, and the like. Further, in some embodiments, cameras may be configured to support on-demand requests for static and motion images submitted by remote parties, such as site owners and supervisors.

It may also be desirable that cameras are weather-insulated as they may be located outdoors and subjected to extreme temperatures, wind and precipitation. Further, each camera preferably may have two independent circuits, so that if one fails the other can serve as a back-up. Similarly, cameras may employ dual, redundant power sources, such that if one power source is unavailable, a back-up power source (e.g., batteries, generators, etc.) may be used. Indeed, in some embodiments, completely autonomous, free-standing image capture hardware may be employed. Such hardware may use solar panels and high capacity energy cells for power, and may use cellular/satellite communications for networking. Such autonomous camera hardware could be used in isolated areas such as deserts and national parks where A/C power is burdensome to obtain.

After the site owners obtain suitable monitoring devices, site owners must register with the system by interacting with the central computer in accordance with the following process steps, which are described as steps performed by the central computer.

Step 1: Receive Request to Register at Least One Monitoring Device.

The central computer receives a request to register at least one monitoring device. The request can be received by the central computer's input device or communication port. Such a communications port or input device may be enabled to receive Dual-Tone Multi-Frequency (DTMF) tones in an Interactive Voice Response (IVR) application. In such an embodiment, site owners would call the central computer via phone, and navigate through an audio menu to complete the registration process. Alternatively, a communications port or input device may be enabled to receive registration commands, via the Internet or other public network, from a computer or monitoring device operated by the site owner.

In a further alternate embodiment, cameras may be equipped with USB or other ports so that registration can take place automatically (i.e., "plug and play") upon the establishment of a connection between the camera's port and the central computer.

Step 2: Confirm Communication with Monitoring Device.

The central computer then sends a test signal (i.e., a "ping") to the monitoring device to confirm its presence and functional ability and, in some embodiments, determine its configuration, location, and other important information.

Step 3: Assign Monitoring Device Identifier and Record Identifier In Site Database.

Once communication with the monitoring device is established, the central computer then assigns a unique identifier to the monitoring device and records the identifier in a record of the site database, such as that which is depicted in Table 1, herein.

Step 4: Initiate Test Procedures.

In some embodiments, test procedures may be instituted to confirm the monitoring device's ability to detect (i.e., to capture images) as intended. For example, the site owner may be instructed by a supervisor, via a two-way audio communication channel, to adjust a camera so as to enable the widest possible field of view, or to reposition a camera angle to eliminate public areas that cannot be considered no-man zones.

Step 5: Receive and Record Site-Specific Rules in Site Database.

In some embodiments, site owners may be prompted to select or otherwise indicate site-specific rules for monitoring. Further, in some embodiments, site owners may be charged premiums for certain levels of service. For example, site owners desiring more or higher levels of security may request lower thresholds or triggers for supervisory review of images. Or, for example, site owners may desire to have at least two "5 star" rated Guardians assigned to monitor images from their site at all times. Such site-specific rules may be recorded in the record corresponding to the assigned monitoring device identifier in the site database, such as that which is depicted in Table 1, herein. Likewise, custom or standard emergency procedures may be similarly identified and recorded for future reference by the system, its operators or Guardians.

In yet other embodiments, site owners and/or monitoring devices may be prompted to capture reference images for later comparison by the monitoring device and/or the central computer against subsequently captured images.

TABLE 1

Site Database

| Monitoring device identifier(s) | Site | Contact information | Monitoring rules | Emergency procedures | Billing information |
| --- | --- | --- | --- | --- | --- |
| 1234-56789, 1234-56790, 1234-56791, 1234-56792 | Smith Memorial Airport, Town, Ohio, USA | Bob Johnson, Security Officer, cellular phone number (212) 555-1212 | Guardians must be located at least 50 miles from site Guardians must be rated 3 or higher | First, confirm emergency with at least 5 other randomly recruited Guardians. Then contact Bob Johnson directly via automated outbound IVR call to listed cell phone number. Then contact local police at (212) 555-9999. | $1000 per month, billed monthly from Bank Account Number 654987987645 |
| 3333-92931, 3333-92932, 3333-02033 | City Hydraulic Company, City, Texas | Nancy Simmons, Water Purity Specialist, pager number (888) 222-2222 | Guardians must always be assigned completely randomly. Guardians should never receive image from this camera twice. | If security threat is detected by at least two Guardians, request supervisor review of subject image. | $1200 per month, billed monthly from Bank Account Number 5879462865832 |

Guardian Registration

In one embodiment, Guardians register with the central computer in order to participate in monitoring sessions and thereby earn compensation for such participation. Registration may take place in accordance with the following process.

Step 1: Receive Registration Request from Potential Guardian.

A potential Guardian transmits to the central computer, via a user device such as a personal computer, cell phone or kiosk, a request to register as a Guardian. For example, a potential Guardian may log on to a website associated with the central computer and click on a hyperlink to indicate the potential Guardian's desire to register.

Step 2: Prompt Potential Guardian for Required Information.

The central computer may then retrieve from memory a list, a "fillable" form, an IVR menu, or other data structure prompting the potential Guardian to input certain required information. The information required may include unique identification data such as a Social Security Number (SSN), a driver's license number, a financial account identifier (credit card account number, debit/checking account number, PayPal® account identifier, etc.), a biometric identifier (e.g., fingerprint), or the like. Further, in order to proceed, the Guardian may be required to answer certain questions, take an oath, agree to the terms of a contract, or otherwise provide assurance that access to the system will not be used for other than its intended purpose. Any or all of such information may be recorded in the Guardian database or elsewhere for future reference.

At this point, based in part on the received information, the central computer may, in some embodiments, initiate a subroutine designed to institute a "background check" of the potential Guardian. Such a subroutine may involve a confirmation of the existence of certain information in remote databases, directly or indirectly accessible to the central computer via a communications port. For example, if a driver's license number is required, the central computer may output a request to a computer operated by a state's licensing authority (e.g., the Connecticut Department of Motor Vehicles) to confirm the validity of the driver's license (i.e., that the license was validly issued and that the name matches that of the potential Guardian). If the results of a background check subroutine indicate that inaccurate or incomplete information was submitted by the potential Guardian, the process may terminate at this point. Otherwise, it may continue.

Step 3: Output Instructional Data.

The central computer may then retrieve from memory and output to the potential Guardian's user device instructional data for the purpose of educating the Guardian about how to participate in monitoring sessions. Such data may take the form of (1) text, (2) audio, (3) video, or (4) any combination thereof. The content of such data may include, for example, instructions about how to respond to images and questions about images.

Step 4: Initiate Testing Subroutine.

The central computer may then, in conjunction with user device, proceed to initiate a testing subroutine for the purpose of ensuring that the potential Guardian (1) witnessed and understood the instructional data, and/or (2) can perform with a certain minimum level of competency in a test ("mock" and/or "live") Guardian session.

In embodiments where the testing subroutine is designed to confirm the potential Guardian's comprehension of instructional data, questions may be retrieved from memory and output to the potential Guardian, who would in turn indicate answer choice selections to the central computer via the user device. The central computer could then compare the received answer selections to a stored set of correct answer choices, determine a score, and compare the score to a stored rule indicating a certain minimum required score. If the potential Guardian's score meets or exceeds the minimum required score, the process may continue. Otherwise, it may end or return to any earlier point (e.g., with the output of instructions).

In embodiments where the testing subroutine is designed to determine whether or not the potential Guardian can perform in a "mock" Guardian session with a minimum required level of competency, the central computer can retrieve and output a stored sequence of test images and questions. The test subroutine would thus determine if, for example, the Guardian can spot humans in no-man zones. Alternatively, a competency test may wholly or partially include "live" images received in substantially real-time from a remote monitoring device. In any event, the potential Guardian's responses are evaluated to determine their accuracy and/or conformance to a central tendency (e.g., mean, median, mode, etc.) of a plurality of responses (e.g., from other Guardians or potential Guardians). If the potential Guardian has performed in accordance with a minimum required level of competency, the process may continue. Otherwise, it may end or return at an earlier point (e.g., with the output of instructions or with the initiation of another testing subroutine).

It should be noted that the instructional subroutine of Step 3 and the testing subroutine of Step 4 may be combined to form an interactive training session.

Step 5: Create Record for Guardian in Guardian Database.

The central computer then creates a record for the potential Guardian in a Guardian database, such as that which is depicted herein in Table 2. In creating such a record, the central computer may generate, assign and record a unique Guardian identifier to the Guardian that may be used to track a given Guardian's participation in monitoring sessions so that records can be kept for rating and compensation purposes. Information that was received from the potential Guardian in Step 1 may be recorded in this Guardian database (e.g., SSN, driver's license number, financial account identifier, biometric identifier). The central computer may also request, receive and record other information from the Guardian that may be useful for future tracking, identification, security, compensation, regulatory compliance and/or tax (e.g., withholding) purposes.

TABLE 2

Guardian Database

| Guardian identifier | Current Guardian rating (1-5) | Guardian identification information | Guardian financial account identifier | Time Logged this Pay Period |
|---|---|---|---|---|
| ABCDEFG | 5 | Bob Schneider 2 Main Street Town, USA | Visa ® Check Card 8888-8888-8888-8888, Exp. | 18 hours, 29 minutes |

TABLE 2-continued

Guardian Database

| Guardian identifier | Current Guardian rating (1-5) | Guardian identification information | Guardian financial account identifier | Time Logged this Pay Period |
|---|---|---|---|---|
| | | State Driver's License # 9999999 SSN 999-99-9999 | 5/07 | |
| ABNGUYC | 4 | Tom Meyer 32 Park Avenue City, USA State Driver's License # 7K1945 SSN 333-33-3333 | Checkin Account Number with ABA Routing Code: 706001 1220012 4563271 | 3 hours, 15 minutes |
| MGNWOIQ | Temporarily banned from system until retraining completed | Mary Sullivan 913 Broadway Village, USA State Driver's License # MS 1902 SSN 222-22-2222 | PayPal ® Account Number 12536 | 47 minutes |

Step 6: Enable Download of Guardian Software to User Device.

After a potential Guardian has achieved the status of "Guardian" by passing all instituted security and competency checks and receiving a Guardian identifier, the central computer enables the Guardian's user device to download any appropriate software necessary to participate in monitoring sessions. In some embodiments, any required cryptographic keys may be downloaded to the user's device. Techniques and protocols enabling the downloading of software applications is well-known to those in the art and need not be described in detail herein.

EXAMPLE

The owners of a nuclear power plant, a privately-owned water reservoir, and an airport each register with the operator of the disclosed system (in this example, named "U.S. HomeGuard") by (a) purchasing cameras, (b) installing them at certain "no-man" zones on the sites' grounds, and (c) participating in an initialization sequence whereby the installed cameras receive Internet Protocol (IP) addresses and capture "reference" images that the system subsequently can use in determining whether to transmit a given image to Guardians.

Independently, U.S. HomeGuard recruits a plurality of Guardians to monitor select still images of the no-man zones and report potential security breaches. Guardians may register with the U.S. HomeGuard system by (a) logging on to a central website, (b) providing certain required background information, (c) downloading operational software, and/or (d) receiving identification information such as unique alphanumeric user identifiers.

After registration, Guardians may log on to the U.S. HomeGuard site at any time and participate in the remote monitoring of select no-man zone images captured by the cameras. So as to reduce the number of transmitted images to only potential security breaches, the central computer or the cameras themselves may be configured to only transmit images to Guardians if there is a triggering activity, such as the triggering of a motion detector circuit and/or the determination that a given image does not match stored reference images.

Once captured, images may be routed to Guardians according to stored rules. Such rules may require, for example, that images are (i) transmitted to a threshold number of Guardians (e.g., at least three Guardians), (ii) assigned randomly to Guardians, (iii) routed according to geographical rules (e.g., that Guardians must be physically situated at least 250 miles from the given no-man zone), (iv) assigned to Guardians based on Guardian ratings (e.g., at least one top rated Guardian receives the image), and/or (v) any combination thereof. Such rules would function to enhance the quality of the monitoring service by allowing for redundancy (i.e., by requiring multiple viewers). Such rules would also function to bolster the security of the system by making the routing of feeds unpredictable (i.e., based on randomness) and/or by maintaining site anonymity (i.e., by routing images based on geographical rules).

Once the Guardians receive images, they are prompted by a user device to indicate if they (1) see a person/vehicle in the picture, (2) do not see a person/vehicle in the picture, or (3) are not sure. The U.S. HomeGuard central computer may maintain a stored set of rules for determining whether a threshold number of responses are received that indicate a potential security threat. If a potential security threat is reported, the central computer may initiate emergency procedures, including verification of the emergency by other Guardians and/or trained professionals, and/or the dispatch of local emergency responders to the site.

The attentiveness of the Guardians can be tested so as to ensure quality of the monitoring service. For example, a data storage device accessible by the central computer may route to Guardians previously-recorded images that depict real or fabricated security breaches in order to determine whether or not Guardians are paying attention to the routed images. Should Guardians fail to report such "false positives" by indicating the correct response, the central computer may (1) adjust a rating associated with the Guardian, (2) adjust the compensation due to the Guardian, and/or (3) temporarily or permanently disable the Guardian from participating in the system.

After viewing images, Guardians may log off at will, and may be compensated for their work. Compensation may be determined based on, for example, (i) the amount of time spent monitoring, and/or (ii) the degree of a given Guardian's responsiveness to real or fabricated security breaches. Compensation may take the form of, for example, a credit to a financial account associated with the Guardian, such as a credit card account, a debit card/checking account, or a service account (e.g., an account for services rendered by an Internet Service Provider).

Monitoring Sessions

Registered Guardians can initiate monitoring sessions at any time. That is, they need not have previously scheduled a monitoring session.

Step 1: Receive Request to Initiate Session.

Monitoring sessions begin when a Guardian sends a request to the central computer to initiate a monitoring session. In some embodiments, various security protocols are employed to ensure that only registered Guardians participate in monitoring sessions. For example, Guardians may be require to submit their Guardian identifiers that were distributed during the Guardian registration process. Guardian identifiers may be submitted without active involvement on the Guardian's behalf, for example, as may happen if the Guardian's user device stored a "cookie" file, accessible to the central computer, that contained the Guardian's identifier. Further, Guardians may be required to submit verifiable passwords in a manner known in the art. Indeed, any level of security desirable and known in the art may be employed.

At this point, a subroutine may optionally be employed to verify the coordination and attentiveness of the Guardian. For example, the central controller may administer, in conjunction with the Guardian's user device, a simple test of the user's coordination (e.g., by requiring the user to trace a line with the mouse cursor) or of the user's reaction time (e.g., by requiring the user to depress the Enter key immediately after seeing an image of a human). Such a test may be useful in determining whether or not the Guardian is currently in an appropriate (i.e., sober, rested) state to participate in a monitoring session.

Alternatively or additionally, the central computer may employ yet another subroutine to determine if the Guardian is temporarily or permanently banned from the system. More specifically, the central controller may use the submitted Guardian identifier to retrieve Guardian rating information from the Guardian database and determine whether or not the Guardian is temporarily or permanently banned from the system. For example, referring to the third exemplary record in Table 2, Mary Sullivan may be banned from the system until she successfully completes a retraining routine similar or identical to that which is disclosed in Steps 3 and 4 of the Guardian registration process. Should a Guardian be temporarily or permanently banned from participating in monitoring sessions, the central computer may direct the Guardian to participate in retraining or may end the process, as appropriate.

Step 2: Identify Captured Data (i.e., Image).

Previously, substantially simultaneously, or subsequently, the central controller may identify an image (or other data) that is available for Guardian review.

In some embodiments, monitoring devices such as cameras may have previously or substantially simultaneously captured images or other data and transmitted such data to the central computer. Monitoring devices may be configured to automatically capture and transmit such data upon the happening of a "triggering" or "image capturing" event, such as (1) the initiating of a motion detector circuit, (2) the detection of thermal changes in a camera's field of view, and/or (3) the detection of a mismatch between a captured image and a previously stored reference image.

In an alternate embodiment, an acoustic perimeter intrusion detection (APID) system may be used to trigger the capture of images. APID systems, such that which is manufactured by ESCI International, Inc. of Clifton, N.J., include one or more metal wires attached to physical ballast dampeners operatively connected to a computer. The wires are attached on or adjacent to a physical fence, and the computer monitors the wires for acoustic vibrations. If vibrations are detected, the computer locates the exact position of the intrusion by monitoring the vibrations on the fence and determining the time that the signals are received from several locations. Such a detected intrusion may in turn trigger the capture and routing of images in the inventive system.

In some embodiments, when an image capture event occurs, the camera hardware may post one (or more) images to the central computer and may also isolate and index a full-motion image buffer (of configurable duration before and after the triggering event) and preserve this buffer in local or remote storage for a finite time period (e.g., 48 hours).

Also, in some embodiments, the central computer may queue the captured image(s) in a routing database, from which images are retrieved and routed to Guardians as described in the following step.

Step 3: Route Data to at Least One Guardian.

After the central computer identifies the data, the data is routed to at least one currently active Guardian for review. In some embodiments, the central computer may route the data to Guardians randomly, based on stored rules, or a combination of both. As disclosed herein, stored rules may be site-specific rules selected by the site owner (see, e.g., columns 4 and 5 of Table 1.).

Alternatively or additionally, the central computer may be configured to impose certain routing rules to ensure quality and security, as discussed herein. For example, the system may require a minimum level of Guardian redundancy. That is, the central computer may require that a minimum number of Guardians review a given image. Further, the central computer may dynamically (i.e., periodically or continuously) adjust such rules for any or all sites based on (1) the number and quality of available Guardians at any point in time, and/or (2) a "threat level" obtained from a remote database, such as one maintained by the United States Department of Homeland Security.

In some embodiments, the routing of captured images includes the routing of response instructions and/or possible answer selections. For example, Guardians could be prompted to indicate if they (1) see a person in the picture, (2) do not see a person in the picture, or (3) are not sure. Alternatively, Guardians could be presented with two images (i.e., one prerecorded reference image and one subsequently captured image) and asked whether or not the two images are a match.

Additionally or alternatively, the central controller may at this step retrieve a false image from a database and transmit the false image to at least one Guardian. The central controller may be configured to transmit false images (1) randomly, and/or (2) periodically, based on stored rules (e.g., every X images, every Y minutes).

Step 4: Identify Response(s).

Guardian responses are then transmitted to and received by the central computer. In some embodiments, if an image is presented to a Guardian and a response is not subsequently received by the central computer within a given time interval, the image "response instance" is redistributed to another Guardian meeting the routing rules for the given image. That is, the image may be transmitted to another Guardian.

In yet other embodiments, if an image is not voted on by the minimum number of Guardians within an overall expiration time interval, the image may be routed to supervisors or otherwise processed in accordance with site-specific rules.

Step 5: Evaluate Received Response(s) and Process Accordingly.

If responses indicating a potential security breach exceed a site-specific threshold (e.g., 2 out of 3 Guardians indicate that there is a human in a no-man zone), certain procedures may be implemented depending on site-specific or general system rules. For example, if a threshold number of Guardians report a human in a no-man zone, the subject image can be routed to one or more Guardians for confirmation (e.g., Guardians with higher ratings), routed to one or more supervisors for confirmation, and/or routed to the site owner for confirmation.

Alternatively or additionally, should a potential security breach be detected, the central computer may enable a two-way audio and/or video communication channel to the corresponding site so that a supervisor can talk to any person in the camera's proximity. In such an embodiment, the supervisor would have the ability to initiate a challenge/response (or "stand down") procedure by asking the person questions that may indicate their authority to occupy the given space (e.g., passwords).

In yet another alternate embodiment, should a potential security breach be detected, the central computer may dispatch local emergency responders and/or contact the site owner. The central computer may further route any relevant captured images to the emergency responders and/or site owner via, for example, a high-bandwidth handheld device such as a 3G enabled cellular telephone. Further, the central computer may activate: (a) an electric fence, (b) an alarm, and/or (c) other site-specific devices and procedures.

Further, site-specific rules may dictate that any or all of the following occur in the event of a potential security breach: (1) all cameras corresponding to the relevant site may immediately capture images, post images for review, and cache full-motion buffers regardless of motion detection status; (2) the cameras that provided the original image(s) may be instructed to upload the motion image buffer(s) associated with the original image to the central computer, which will make these buffered images available to supervisors and/or emergency responders as needed; and (3) a site alert may be created and posted to a site incident portfolio for Supervisor review.

In embodiments where the central controller transmitted at least one false image to at least one Guardian, the relevant Guardian's response may be evaluated. The system may compare the Guardian's response against a stored set of correct or preferred answers, and inaccurate or undesirable responses may lead to negatively adjusted ratings, as discussed with reference to the next step.

Step 6: Adjust Guardian Rating Based on Evaluation of Received Response(s).

As discussed herein, Guardians can be categorized according to their current skill level (determined by their performance in evaluating real and false images). In some embodiments, Guardians in good standing may be given a numerical score and Guardians who are temporarily or permanently banned from participating in monitoring sessions may be so marked in corresponding database records (see, e.g., Table 2).

According to an alternate rating scheme, a Guardian can be in "good standing", "on probation", "suspended", or "banned". The scoring thresholds that define the category boundaries can be configured at the site level. The rules defining the effect of a status and the requirement for moving out of a status can be defined system-wide and overridden at the site level as necessary. Example rules include (a) a "good standing" Guardian may receive real (i.e., live) images and test images according to stored image routing rules, (b) a Guardian who is "on probation" may only receive test images until their score moves them back into the "good standing" category (this category might be initially in effect for new Guardians); (c) a Guardian who is "suspended" may need to take a remedial on-line training course and pass it to move into the "on probation" category, (d) a Guardian who is "banned" would not be allowed back on the system.

Step 7: Receive Request to Terminate at Session.

At any time, a Guardian may unilaterally end his or her participation in a monitoring session by transmitting to the central server a signal so indicating.

It should be noted that, in an alternate embodiment, the step of adjusting Guardian ratings (Step 6) may take place after the step of receiving a request to terminate the session (Step 7).

Step 8: Calculate and Initiate Provision of Compensation to Guardian.

The central computer system may then determine the amount of compensation due to a Guardian and initiate the provision of compensation. Guardians may be afforded different pay rates according to their rating status. For example Guardians rated at "5" may receive a rate of $8/hour, while Guardians rated at "4" may receive a rate of $7.50/hour. In such an embodiment, the central computer would multiply the amount of time logged by the Guardian by the given Guardian's pay rate. This could be done after each Guardian session, or, alternatively, could be done periodically (e.g., weekly, monthly) or upon the Guardian's request.

The central controller may initiate payment by instructing that an account associated with the Guardian be credited. Methods for crediting accounts and transferring funds are well known and need not be described in detail herein.

Alternate payment mediums are contemplated, as discussed herein with reference to the section entitled "Additional and Alternate Embodiments".

Additional Embodiments

In some embodiments, the probability of a Guardian receiving a test image instead of a live image may be driven by a calculation that increases the probability in inverse proportion to their current accuracy rating.

In some embodiments, test images may be categorized for degree of difficulty and this degree of difficulty may "weight" a Guardians score when they submit responses associated with these images.

In some embodiments, test images may be categorized by visual characteristics (e.g., snow, water effects, low light, wide angle) and a scoring engine may be used to increase the probability of a Guardian scoring well in that category getting a site image that matches these characteristics.

In some embodiments, image routing and escalation rules may ultimately be driven be an artificial intelligence network and/or a cognitive rules engine.

In some embodiments, Guardians who have previously reviewed images for a particular site can be assigned a higher or lower probability of reviewing an image from the same site (or they may be excluded completely).

In some embodiments, test images may be given accompanying "answer" images that highlight the part of the image that contains a person (for false positives) or explain that there is no person (for false negatives) and this "answer" image may be presented to the Guardian immediately after erroneously voting on the test image.

In yet another alternate embodiment, site anonymity can be further maintained by employing stored rules that function to actively suppress the transmission of location-specific information from the Guardians. For example, using artificial intelligence, the system may pre-screen all images and redact any text therein (e.g., signage), so that information relevant to the site's location is not transmitted to the Guardians.

In some embodiments, supervisors may access the system via a supervisor interface that may be a highly secure internet-accessible (e.g., SSL browser w/RSA authenticated VPN connection) tool used to manage, prioritize and resolve site alerts.

In some embodiments, the supervisor interface can enable the supervisor to adjust PTZ orientation of any camera, and can enable the supervisor to engage in two-way audio communication via appropriately configured image capture nodes.

In some embodiments, supervisors can schedule planned maintenance outages for monitoring devices.

In some embodiments, the supervisor interface may present all captured images related to a site incident file. These images will be provided in both full resolution and thumbnail for quick reference.

In some embodiments, the supervisor interface can enable Supervisors to access and review the full motion image buffers surrounding alert images from all sites and monitoring devices.

In some embodiments, the supervisor interface can enable supervisors to access real-time full motion images from any monitoring device.

In some embodiments, supervisors can adjust motion sensor zones and sensitivity for monitoring devices.

In some embodiments, when Guardians and Supervisors register with the system they will be asked to record a number of confidential question/answer pairs related to their personal information. In addition to secure site password login, these questions will intermittently be posed to Guardians/Supervisors when they log in as a means of supplemental authentication. The requirement for and frequency of this authentication can be configured at the site level for Supervisors and can be driven by score and/or status for Guardians.

In some embodiments, supervisor authentication security may be supplemented by a hardware-based key generation device (e.g., RSA key fob).

In some embodiments, multiple redundant core data centers may be employed.

In some embodiments, all Guardian access may be via authenticated SSL browser connections.

In some embodiments, a "single sign-on" rule will be enforced for Guardians so that Guardians cannot participate in two monitoring sessions simultaneously.

In some embodiments, anti-fraud check logic may be used to prevent re-establishment of banned Guardians (personal and financial data matching algorithms, network usage patterns, etc.).

In some embodiments, administrators will access the supervisor interface via a browser through secure network tunnels (e.g., authenticated VPN connections).

In some embodiments, Guardian compensation levels may be adjusted by local hour of the day to promote participation during periods of low Guardian on-line activity (e.g., 1-5 AM EST).

In some embodiments, Guardians may be compensated in the form of tax credits. For example, Guardians may be offered an alternative way to pay their federal income taxes by participating in the system. In such an embodiment, Guardian SSNs will be used to track such earned tax credits.

Similarly, prisoners may be afforded the opportunity to earn "good behavior" credit by participating in monitoring sessions.

In some embodiments, Guardians may be compensated by being offered the chance to win a sweepstakes prize. In such embodiments, a game may be incorporated into the monitoring session program. For example, Guardians who view and report winning game pieces in images may receive a prize. Such sweepstakes would encourage attentiveness and provide a different form of economic motivation.

Further, Guardians may be rewarded with bonuses or enhanced compensation for spotting real emergencies.

In some embodiments, all remote monitoring devices will receive a "heartbeat ping" (i.e., a query) issued by the central computer at a configurable interval. Devices that do not respond may immediately trigger the initiation of emergency procedures.

In some embodiments, at an interval defined at the site level, the monitoring devices will be instructed to post a static image regardless of motion detection status. This image can be analyzed by the image processing network and compared to the last image from the same device to determine if significant composition change has occurred that would imply movement and, if so, route the image for Guardian review. The sensitivity of this analysis can be site or device specific.

Rather than physical property, Guardians could monitor complicated computer systems, and the monitoring device could be some type of software analysis of network patterns, rather than a camera. For example, no accesses of a certain type should be made, and the system can graphically represent such accesses for ease of analysis by Guardians. This type of monitoring could be done by Guardians who possess certain basic computer skills.

Similarly, the system could be configured to monitor sounds. Relatively unskilled Guardians could distinguish mundane sounds from, e.g., shouting, cries for help or gunshots. In one embodiment, sound monitoring (which is very low bandwidth) could be used in conjunction with image monitoring to direct images of certain sites to more Guardians. This works especially well even in sites which are not strictly 'no-man' zones.

In some embodiments, cameras may be mobile or mounted on mobile vehicles (cars, trucks, unmanned flying drones, etc.) to enable monitoring of a plurality of sites. Again, sites need not be no-man zones. For example, cameras may be mounted on a patrol vehicle, and Guardians could monitor an area much better while the driver conducts a foot patrol.

In some embodiments, a subset of monitoring devices may be randomly or otherwise activated/deactivated at a given time based on the number and/or quality of available Guardians. Such an embodiment would function to increase the level of security at times when there are more cameras than active/qualified Guardians.

In some embodiments, site owners may be charged based on the number of images actually reviewed by Guardians in a given amount of time.

In some embodiments, cameras configured at highly or densely populated areas (ATMs, toll booths, shopping malls, etc.) and Guardians may actually be asked to compare still images of human subjects captured from such cameras against a reference image of a particular human in order to determine if there is a "match". For example, Guardians could log on and compare, one by one, the many captured images taken from the millions of security cameras nationwide against a given picture of a fugitive or a missing person. Guardians could simply indicate "match" or "no match". Thus, the abundance of captured images that may contain the fugitive or missing person could be viewed by Guardians in hopes that fugitives could be caught and missing persons located. In the rare event that a match is detected, the date, time and position of the image-capturing camera can be used to reconstruct the subject's trail and isolate the subject's whereabouts.

ADDITIONAL EXAMPLES

The following examples illustrate various embodiments of the invention which may be advantageously employed to achieve various utilities.

When an image capture event occurs, the image capture node hardware will post one (or more depending on configuration) images to the image services network and will also isolate and index a full-motion image buffer (of configurable duration before and after the triggering event) and preserve this buffer on local storage for a finite time period (optimally 48 hours, configurable).

The image services network will pre-process the image and post the image review request to the routing database.

The image routing database will present the image to the next appropriate Guardian that makes an image request, based on distribution quantity and routing rules (site/node configurable).

If an image is presented to a Guardian and is not subsequently voted on within a (site/node configurable) time interval that Guardian's vote is invalidated and the image "vote instance" is redistributed.

If an image is not voted on by the minimum number of Guardians within an overall expiration time interval (site/node configurable) the image may be escalated according to site rules.

Guardian votes are posted and processed by a vote management service.

If affirmative votes exceed a site/node defined threshold the image is escalated according to site rules.

Site escalation rules may dictate that any of the following occur during image escalation:

Image goes through a second wave of distribution to Guardians based on routing logic defined for that escalation level (e.g., to Guardians with higher average accuracy scores).

All image capture nodes for escalated site immediately register capture events, post images for review, and cache full-motion buffers regardless of motion detection status.

Image capture nodes that provided the original image(s) undergoing escalation will be instructed to upload the motion image buffer(s) associated with the original image to the image services network which will make these buffered images available to Supervisors as needed.

When appropriate escalation level is reached, a site alert is created and posted to a site incident portfolio for Supervisor review.

The site supervisor module will execute any appropriate automated alert notification processes defined for the site (e.g., page, email, cell notification w/image).

Supervisors can "stand down" image escalation at any level and close out site alerts and site incident portfolios.

The system will archive/purge static and motion images associated with closed alerts in accordance with site-defined rules.

Raw images posted from image capture nodes will be optimized for Guardian review through an image processing service that will do things such as grayscale the image, enhance brightness & sharpness, etc. The pre-processing software can be configured at the site/node level to tune it to the visual characteristics of a particular node (e.g., heavy sun glare at certain hours). The "raw" (pre-processing) image may be retained for a site-defined time period and is then discarded.

All processed images are given a unique index number that associates them with the source site/node.

All processed images have a digital watermark injected and a digital fingerprint is taken of the image (e.g., via an MD5 checksum) to facilitate authentication of the image in its final form.

After being processed, images are posted to a content distribution network to facilitate image fetch load distribution.

Guardians who have previously reviewed images for a particular site/node can be given higher or lower probability of reviewing an image from the same site/node (or they may be excluded completely).

Test images have accompanying "answer" images that highlight the part of the image that contains a person (for false positives) or explain that there is no person (for false negatives) and this "answer" image is presented to the Guardian immediately after erroneously voting on the test image (before any available live images are presented).

The probability of a Guardian receiving a test image instead of a live image may be driven by a calculation that increases the probability in inverse proportion to their current accuracy rating.

Test images may be categorized for degree of difficulty and this degree of difficulty may "weight" a Guardians score when they vote on these images.

Test images may be categorized by visual characteristics (e.g., snow, water effects, low light, wide angle) and a scoring engine may be used to increase the probability of a Guardian that scores well in that category getting a site image that matches these characteristics.

Image routing and escalation rules may ultimately be driven be an AI/Bio network and/or a cognitive rules engine of some kind (though initially will be driven by a meta-data rule base—the prototype uses logic coded in database stored procedures and tables).

Guardians can be categorized according to their current skill level (determined by their performance in evaluating seeded test images). A Guardian can be in "good standing", "on probation", "suspended", and "banned". The scoring thresholds that define the category boundaries can be configured at the site level.

The rules defining the effect of a status and the requirement for moving out of a status can be defined system-wide and overridden at the site level as necessary. Example rules might be:

A "good standing" guardian receives live images and test images according to the image routing logic engine's determination.

A Guardian who is "on probation" only receives test images until their score moves them back into the "good standing" category. This category might be initially in effect for new Guardians.

A Guardian who is "suspended" would need to take a remedial on-line training course and pass it to move into the "on probation" category.

A Guardian who is "banned" would not be allowed back on the system.

When Guardians and Supervisors are set up on the system they will be asked to record a number of confidential question/answer pairs related to their personal information. In addition to secure site password login, these questions will intermittently be posed to Guardians/Supervisors when they log in as a means of supplemental authentication. The requirement for and frequency of this authentication can be configured at the site level for Supervisors and can be driven by score and/or status for Guardians.

Supervisor authentication security may be supplemented by a hardware-based key generation device (e.g., RSA key fob).

Guardian compensation levels may also be adjusted by local hour of the day to promote participation during periods of low Guardian on-line activity (e.g., 1-5 AM EST).

The site supervisor interface is a highly secure internet-accessible (e.g., SSL browser w/RSA authenticated VPN connection) tool used to manage, prioritize and resolve site alerts.

The interface presents all image capture node images related to a site incident profile. These images will be provided in full resolution and thumbnail for quick reference.

The interface can enable Supervisors to access and review the full motion image buffers surrounding alert images from all site image capture nodes.

The interface can enable supervisors to access real-time full motion images from any site image capture node.

The interface can enable the supervisor to adjust PTZ orientation of any node camera, and can enable the Supervisor to engage in two-way audio communication via appropriately configured image capture nodes.

Supervisors can schedule planned maintenance outages for nodes and establish ongoing hours of operation for nodes.

Supervisors can adjust motion sensor zones and sensitivity for image capture nodes.

Driving parameters for escalation rules are maintained by the site supervisors through this interface (e.g., votes needed for escalation, escalation path, etc.).

Alert data and images may be dispatched from the supervisor interface to remote parties via electronic means (e.g., cell phone, email, etc).

Granular role-based permissions can be enforced on all site supervisor functionality.

Camera and supporting peripheral hardware used in image capture nodes will have embedded computer devices and will support various standard internetworking and operating system protocols (e.g., embedded Linux chips that support HTTP, SSL, FTP, CGI, Java, etc.).

The prototype is being developed using Axis camera hardware (2420 series network cameras with IR lens, 250-S MPEG-2 network video servers, 2191 audio modules). All this node hardware features embedded Linux chips and open protocols as described above (though no SSL or Java off-the-shelf). The prototype cameras & peripherals are networked using wireless bridges—the wireless interface would optimally be on-board (as an add-in capability to save cost when not needed).

Camera hardware located outdoors will be housed in protective covering and will be hardened to tolerate temperature extremes.

Camera hardware may be equipped with IR lenses for low-light image capture.

Camera hardware may be equipped with PTZ (Pan/Tilt/Zoom) mechanisms to facilitate remote adjustment of field of view, focus, etc.

Image capture node hardware will support on-demand requests for static and motion images submitted by remote services (such as the site administrator module).

It may be possible to implement completely autonomous, free-standing image capture hardware that uses solar panels and high capacity energy cells for power and cellular/satellite communications for node networking (These could be used in isolated areas such as deserts and national parks).

Image capture node networking may include use of 802.11b & related wireless protocols.

Image capture node networking may include use of cell networks (GSM and other emerging standards).

Multiple redundant core data centers will form the backbone of the services layer.

A content distribution network (numerous distributed nodes) will be used for image distribution.

All Guardian access will be via authenticated SSL browser connections.

Single sign-on will be enforced for Guardians.

Anti-fraud check logic will be used to prevent re-establishment of banned Guardians (personal & financial data matching algorithms, network usage patterns, etc.).

Administrators will access the supervisor interface via browser through secure network tunnels (e.g., authenticated VPN connections).

DOS attacks (e.g., spoofing and flooding of Guardian image votes) will be a significant concern. Anti-spoofing measures will be implemented to disregard forged image requests and vote responses before they are processed by the appropriate services. Examples of these might be network pattern analysis engines that identify and suppress redundant image requests and vote responses.

All site image capture notes will receive a heartbeat ping issued by remote management services at a configurable interval. Nodes that do not respond will immediately generate a site alert and incident portfolio and alert will trigger appropriate escalation as defined by the site rule base.

At an interval defined at the site/node level the image capture nodes will be instructed to post a static image regardless of motion detection status. This image can be analyzed by the image processing network and compared to the last image from the same node to determine if significant composition change has occurred that would imply movement and if so process the image for Guardian review. The sensitivity of this analysis can be site/node configurable (if need be all health snapshots can be submitted for review).

Definitions

The following definitions are used herein above, unless otherwise indicated.

Central computer, central controller, central server, server—A computer or computing device, which typically comprise at least one or more of: (i) a processor, such as one based on the Intel® Pentium® series processor, (ii) a means for receiving signals from at least one monitoring apparatus, (iii) a means for transmitting signals to at least one user computer, and/or (iv) a data storage device/memory. For example, the central computer may be one or more IBM E-series™ servers.

False positive, false image, fabricated image, fabricated security breach—an indication which, if transmitted to a Guardian, should to elicit a positive response. For example, the false positive may be a pre-recorded image or other data file depicting a real or fictitious site or no-man zone.

Guardian—A citizen who participates in the remote monitoring of sites, typically in exchange for compensation.

Monitoring apparatus, monitoring device, sensor—A device capable of receiving or generating (e.g., via an input device such as a charge coupled device) a signal indicative of a sensed state (e.g., an image) and data representing the sensed state (e.g., a captured image). A monitoring apparatus may include, e.g., (i) a processor, such as one based on the Intel® Pentium® series processor, and/or (ii) a data storage device/memory. Such sensors include, but are not limited to: (a) digital video cameras, (b) digital video cameras equipped with motion detection and/or "short loop" tripping features, (c) digital cameras, and (d) motion detectors. A monitoring devices may be capable of converting analog signals into digital data files.

"No-man" zone—An area, usually a security-sensitive area on a site, where no humans or vehicles should be monitored (e.g., no humans should be present). No-man zones may include areas adjacent to, within, outside of or otherwise in proximity to sites such as airports, chemical plants, natural gas plants, pipelines and pumping stations, power plants (including nuclear reactors), refineries, and reservoirs.

Site, Remote Site, Property—Property, including but not limited to real property, containing critical infrastructure or other resources which are to be monitored. Such property may be monitored by one or more monitoring apparatus.

Supervisor, Trained Professional, Professional—A supervisor may assist site owners in configuring and initializing monitoring devices. A supervisor may receive certain images after review by at least one Guardian. A supervisor may be, e.g., an employee or agent of the owner/operator of the central computer.

User computer, user device, device—A device capable of (i) receiving a signal (e.g., sensed data) from a central computer and/or a monitoring apparatus, e.g., via a standard Internet connection; (ii) outputting a signal to a Guardian or other user, e.g., via a Web browser displayed on a monitor; (iii) receiving a response from a user, e.g., via an input device such as a mouse, keyboard and standard Microsoft Windows® interface, and/or (iv) transmitting a signal indicative of the response (e.g., a result) to a central computer and/or a monitoring apparatus, e.g., via a standard Internet connection. In some embodiments, a user device may include (1) a processor, such as one based on the Intel® Pentium® series processor, and/or (2) a data storage device/memory. Examples of user devices include appropriately configured personal computers, cellular telephones, and game stations such as the Xbox® and the PlayStation® game stations.

Neuron—a component which is capable of (i) receiving a signal (e.g., sensed data) from a central computer and/or a monitoring apparatus, e.g., via a standard Internet connection; and (ii) transmitting a signal indicative of the result (e.g., based on processing the received signal) to a central computer and/or a monitoring apparatus, e.g., via a standard Internet connection. In some embodiments, a user device may include (1) a processor, such as one based on the Intel® Pentium® series processor, and/or (2) a data storage device/memory. Examples of user devices include appropriately configured personal computers (e.g., a user computer operated by a Guardian), cellular telephones, and game stations such as the Xbox® and the PlayStation® game stations.

Disclosed below are systems and methods facilitating the ad hoc performance of tasks by workers. According to some embodiments, a network of devices is configured to enable individual workers to log on to a central system at any time through devices such as personal computers and cellular telephones and perform low-skill tasks. Such workers may terminate work sessions unilaterally and are compensated based on the amount of work performed.

According to some embodiments, the central system is configured to receive and register task information from at least one employing party. Further, according to some embodiments, the central system is configured to register remote workers. Additionally, according to some embodiments, the central system is configured to manage work sessions. Further still, according to some embodiments, the central system is configured to manage the financial settlement of work sessions, including the billing of an employing party, the compensation of workers, and the allocation of commissions to the operator of the central system. Many additional and alternate embodiments are also disclosed.

In this manner, the systems and methods disclosed herein allow, e.g., low-skill workers to supplement their incomes. Further, the systems and methods disclosed herein allow workers of all skill levels to earn income at heretofore unproductive times by remotely performing low-skill tasks in an ad hoc, fluid manner. Additionally, by enabling the remote performance of ad hoc tasks, the systems and methods disclosed herein allow employers to purchase labor in incremental units that traditionally would not be economically feasible due to travel costs and hourly pay structures.

EXAMPLES

Example 1

An Internet service provider such as America Online® (AOL) has configured its computer system to receive job requests from remote employers via the Internet. A manufacturing company registers with AOL to have digital images of its assembly line process reviewed for irregularities by AOL subscribers. AOL and the manufacturing company agree that the company will pay $5,000 for every 100,000 images viewed by two independent AOL subscribers. The parties also agree that AOL will compensate subscribers as it sees fit. Accordingly, AOL decides to retain $11000 of every $5000 received from the manufacturing facility, leaving $4000 to compensate the duplicative viewing of 100,000 images (i.e., 200,000 images). Accordingly, AOL will thus pay AOL subscribers to view images at the rate of $0.02 per image ($4000/200,000 images=$0.02/image). After the job is registered, AOL then actively advertises the opportunity to its subscribers. As advertised, subscribers would log on to AOL and view digital images of products at a particular stage of an assembly line, one after the other. Subscribers are instructed to click the "OK" or "ERROR" buttons on their screen, depending on whether or not the particular images match a given reference image that represents a high-quality, error-free unit at the given point in the assembly line.

Bill Jones, an AOL subscriber, is a low-wage worker who works a full-time job in a grocery store. One month, Bill is surprised with a $200 unexpected furnace repair bill. Concerned that his current financial resources are insufficient, Bill logs on to AOL with the intent of emailing a relative and asking to borrow $200. However, Bill's attention is drawn to an area on the AOL graphical user interface (GUI) advertising the opportunity to get paid for performing online quality control monitoring. Bill clicks on the advertisement and begins work immediately by comparing the scrolling series of images on the left side of his screen against the "control" or reference image on the right hand side of the screen, entering "OK" if the images match, and "ERROR" if the images are not a match. Over the next few evenings, Bill logs on and reviews a total of 10,000 images and thereby earns $200. Once he reaches his goal, he transmits a request to AOL's server to get paid, and the $200 is immediately credited to his debit/checking account already on file with AOL.

Example 2

A news organization has arranged with Verizon Wireless to pay subscribers for answering survey questions. Mary Johnson, a Verizon subscriber, is a commercial real estate agent working almost entirely on commission. One evening on her way home from work, while reflecting on the recent slump in sales, she is delayed in an unexpected traffic jam.

Her thoughts turn to the rising price of gas, her high mortgage bills, and her son's college tuition. Overwhelmed and frustrated, she decides she must try to make this time productive. However, at 6:00 PM, it's too late catch her clients in their offices. But, she does recall seeing Verizon marketing materials offering the opportunity to get paid for answering survey questions. She puts on her earpiece/microphone unit, presses #WORK (#9675) on the keypad of her cellular phone, and starts answering survey questions by listening to the questions, and responding verbally to prompts from an Interactive Voice Response Unit (IVRU).

For example, the IRVU may output the question "Do you support an increase in the federal income tax to fund increased healthcare benefits for senior citizens? Yes or no?" After deliberating for a moment, Mary responds "no", and the IVRU uses voice-recognition technology to interpret, digitize and record her response. Then, the IVRU may ask "Do you think the income tax on stock dividends should be repealed?" Mary would likewise provide her response. After ½ hour of sitting in traffic, Mary has earned $12, more than enough to pick up dinner for herself and her son on the way home.

Example 3

Jennifer, an America Online subscriber, is a teenager who regularly uses AOL's Instant Messenger to communicate with her friends. While instant messaging, Jennifer earns money by answering survey questions from interested commercial entities such as Old Navy, Abercrombie & Fitch, Capital Records, MTV® and the like. Because she is paid per question answered (rather than hourly), it is perfectly acceptable for her focus to change as she crafts instant messages, fields phone calls, changes radio stations, and the like. She can answer questions when it is convenient for her. For example, while waiting for a friend to respond to an Instant Message, she may answer a survey question in a different window of the AOL GUI.

Definitions

The following definitions are used herein below, unless otherwise indicated.

Ad hoc task, micro-task, micro-work, piecemeal work, piecework, task—A compensable unit of work registered with a central service by an employing party, the performance of which taking place at any time thereafter by a remote worker. Generally, ad hoc tasks are comprised of finite, incremental units of work that together form a broader project or objective for the employing party. For example, a survey may be divisible into many discrete, individually-compensable questions. The division of projects into such micro-tasks facilitates the beginning and ending of tasks in an ad hoc, impromptu manner. For example, because it only takes a few moments to complete a single survey question, a worker who does not have much time may quickly log on, complete a question or two, and then log off. In order to facilitate the impromptu performance of tasks by a wide range of workers during a wide range of times, ad hoc tasks are generally low-skill tasks.

Central computer, central controller, central server, server—A computer comprising at least one or more of: (i) a processor, such as one based on the Intel® Pentium® series processor, (ii) a means for receiving signals from at least one monitoring apparatus, (iii) a means for transmitting/receiving signals to/from at least one worker device, and/or (iv) a data storage device/memory. Generally, central computers are owned, operated and maintained by communications services such as cable, phone and/or Internet services.

Employer device—A computer comprising at least one or more of: (i) a processor, such as one based on the Intel® Pentium® series processor, and/or (ii) a means for transmitting/receiving signals to/from at least one central computer. In some embodiments, employer devices are used to upload information regarding low-skill tasks, including task content and payment terms.

Employing party, employer—A party who registers a task with a central operator and compensates the central operator and/or one or more remote workers for the performance of the task.

Low-skill task—Low-skill tasks are tasks, jobs, or other units of work that require little or no worker credentials and can be performed by providing a simple communication responsive to a transmission of task information. Generally, low-skill tasks are relatively non-imposing when compared to other, more mentally consuming (i.e., higher skill) tasks. Thus, low-skill tasks generally can be performed by workers while workers are engaged in other activities. Further, low-skill tasks generally can be started and stopped quickly and fluidly, without significant "switching cost".

Monitoring device—A device located at a site associated with an employing party that is configured to communicate with a central computer and/or a worker device so that workers can receive site-specific data and perform tasks based on the site-specific data. For example, a monitoring device may comprise a video camera, and a micro-task may involve viewing an image captured by the video camera and responding as to the contents of the image.

Work session—A period of time during which a remote worker performs at least one micro-task. Generally, work sessions include a plurality of micro-tasks.

Worker—A person who communicates, via a worker device, with a central computer and/or a monitoring device for the purpose of earning compensation in exchange for the performance of micro-tasks. Generally, workers need not possess particular skills, as most micro-tasks are low-skill tasks. Further, workers are often subscribers to a communications service such as a cable, phone and/or Internet service.

Worker device, user computer, user device—A device capable of (i) receiving a signal from a central computer and/or monitoring device, (ii) outputting a signal to a user (i.e., a worker), (iii) receiving a response from a user via an input device, and (iv) transmitting a signal indicative of the response to a central computer and/or monitoring device. In some embodiments, a user device may include (1) a processor, such as one based on the Intel® Pentium® series or Centrino® series processor, and/or (2) a data storage device/memory. Example worker devices include personal computers, Personal Digital Assistants (PDAs) and cellular telephones.

Network Configuration

The embodiments described below can be configured to work in a network environment whereby the central computer, the user computer, the employer device, and/or the monitoring device communicate with each other directly or indirectly, via a wired or wireless medium such as the Internet, LAN, WAN or Ethernet, Token Ring, or via any appropriate communications means or combination of communications means. Communication between the devices and computers, and among the devices, may be direct or indirect, such as over the Internet through a Website maintained by a computer on a remote server or over an on-line data network including commercial on-line service providers, bulletin board systems and the like. In yet other embodiments, the devices may communicate with one another and/or a computer over RF, cable TV, satellite links and the like.

Some, but not all, possible communication networks that may comprise the network or be otherwise part of the system include: a local area network (LAN), a wide area network (WAN), the Internet, a telephone line, a cable line, a radio channel, an optical communications line, and a satellite communications link. Possible communications protocols that may be part of the system include: Ethernet (or IEEE 802.3), SAP, ATP, Bluetooth™, and TCP/IP. Further, networking of devices and computers may include use of 802.11b and related wireless protocols and/or use of cell networks (GSM and other emerging standards).

Those skilled in the art will understand that computers and devices in communication with each other need not be continually transmitting to each other. On the contrary, such computers and devices need only transmit to each other as necessary, and may actually refrain from exchanging data most of the time. That is, a device in communication with another device via the Internet may not transmit data to the other device for weeks at a time. For example, a worker may download a project (i.e., a plurality of micro-tasks such as questions) from the central computer to a worker device, perform the micro-tasks piecemeal (e.g., as time permits), and then upload the project results (i.e., answers to questions) when complete.

In an embodiment, a central computer may not be necessary and/or preferred. For example, the present invention may, in one or more embodiments, be practiced on a monitoring device in communication only with one or more user computers. In such an embodiment, any functions described as performed by the central computer or data described as stored on the central computer may instead be performed by or stored on one or more monitoring devices or user computers.

Data Storage Devices/Memory

For each computer and/or device (i.e., the central computer, the user computer, and/or the monitoring apparatus), a processor may be in communication with a memory and a communications port (e.g., for communicating with one or more other computers or devices). The memory may comprise an appropriate combination of magnetic, optical and/or semiconductor memory, and may include, for example, Random Access Memory (RAM), Read-Only Memory (ROM), a compact disc and/or a hard disk. The memory may comprise or include any type of computer-readable medium. The processor and the memory may each be, for example: (i) located entirely within a single computer or other device; or (ii) connected to each other by a remote communication medium, such as a serial port cable, telephone line or radio frequency transceiver.

In one, several or all computers or devices, a memory may store a program for controlling a processor. The processor performs instructions of the program, and thereby operates in accordance with the present invention, and particularly in accordance with the processes described in detail herein. The program may be stored in a compressed, uncompiled and/or encrypted format. The program furthermore includes program elements that may be necessary, such as an operating system, a database management system and "device drivers" for allowing the processor to interface with computer peripheral devices. Appropriate program elements are known to those skilled in the art, and need not be described in detail herein.

The term "computer-readable medium" as used herein refers to any medium that participates in providing instructions to a processor for execution. Such a medium may take many forms, including but not limited to, non-volatile media, volatile media, and transmission media. Non-volatile media include, for example, optical or magnetic disks, such as memory. Volatile media include dynamic random access memory (DRAM), which typically constitutes the main memory. Transmission media include coaxial cables, copper wire and fiber optics, including the wires that comprise a system bus coupled to the processor. Transmission media may carry acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying one or more sequences of one or more instructions to a processor for execution. For example, the instructions may initially be borne on a magnetic disk of a remote computer. The remote computer can load the instructions into its dynamic memory and send the instructions over a telephone line using a modem. A modem local to a particular computer or device can receive the data on the telephone line and use an infrared transmitter to convert the data to an infrared signal. An infrared detector can receive the data carried in the infrared signal and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of carrier waves that carry data streams representing various types of information. Thus, a computer or device may obtain instructions in the form of a carrier wave.

According to an embodiment of the present invention, the instructions of the program may be read into a main memory from another computer-readable medium, such from a ROM. The execution of sequences of the instructions in a program causes the processor to perform the process steps described herein. In alternate embodiments, hard-wired circuitry may be used in place of, or in combination with, software instructions for implementation of the processes of the present invention. Thus, embodiments of the present invention are not limited to any specific combination of hardware and software.

The memory also may store one or more databases. Some or all of the data stored in each database is described in conjunction with the following description of the process steps. The described entries of the databases represent exemplary information only; those skilled in the art will understand that the number and content of the entries can be different from those illustrated herein. Further, despite any description of the databases as tabular, relational databases, an object-based model could be used to store and manipulate the data types of the present invention and likewise, object methods or behaviors can be used to implement the processes of the present invention.

Processes

The following processes are described as routines performed by the central computer. However, it should be understood that such processes may be performed entirely or in-part by other devices, such as those described herein.

Task Registration Process

Step 1: Receive Task Registration Data.

Employing parties register at least one task with the central service by, for example, uploading data to the central computer from an employer device. Such data may be uploaded through a Web-accessible GUI, in accordance with Electronic Data Interchange (EDI) standards and formats, or the like.

Task data to be uploaded may include, but is not limited to: (1) IP addresses to patch through camera feeds, (2) remote file addresses for question content, possible answer choices and/or answer formats, (3) digital files containing information regarding question content and/or answer choice content, (4) financial data, such as compensation rates (for the central service and/or workers), compensation instructions (e.g., payment medium/means) and/or an account number of the employing party (e.g., for automatic billing purposes), (5) instructions for completion of the task, (6) instructions for how a task is to be divided (e.g., an indication of the divisible units of a project), (7) instructions for how and/or when the complete task is to be returned and/or presented to the employer, (8) required/desired worker qualifications (e.g., worker demographics), (9) performance conditions/prerequisites as defined herein.

Step 2: Process Received Task Registration Data.

In some embodiments, received task registration data is processed according to rules included therein or according to stored rules. For example, task registration data may include a complete survey, and the survey may be divided into individual questions. Or, task registration data may include a complete document that needs to be proofread, and the document may be divided into pages, paragraphs, sentences, phrases or words.

Further, in some embodiments, received task registration data may be divided into a given number of task instances according to a numerical minimum or maximum indicated by the employer. For example, an employer wishing to conduct a survey may indicate that questions are to be answered by at least 50 respondents (workers). In this case, a single question can be registered in a task database (described below) fifty times, as fifty separate micro-tasks.

Step 3: Store Task Registration Data in Task Database.

Uploaded task data may be stored in a task database that is consulted in the below-described work session process. An example task database is shown in Table 3 below:

Worker Registration Process

According to some embodiments, workers may be required to register before they are permitted to participate in work sessions.

Step 1: Receive Registration Request from Potential Worker.

According to some embodiments, potential workers may log on to a website hosted by the central computer or otherwise log on to an online service (e.g., an ISP's home page), at which time they may send a request to register as a worker by, for example, clicking on a button.

Step 2: Request Registration Data from Potential Worker.

According to some embodiments, workers may be required to provide certain data to the central computer in order to participate in work sessions as workers. Such data may include (1) contact information (name, address, phone number, email address, etc.), (2) Social Security Number (SSN), (3) demographic information (race, gender/sex, age), and/or (4) financial account identifiers (e.g., credit card account numbers, debit card account numbers, checking account numbers, etc.).

The central computer may prompt or otherwise request any or all of such data from the potential worker after Step 1. Alternatively, such data may be previously registered with the central computer, as may be the case where the central computer is a computer operated by an Internet Service Provider and the potential worker is already registered as a customer of online services. That is, consumers who are registered with the central service as a subscriber/customer may already have some or all of the requisite registration data on file with the central computer. (See, e.g., Examples 1, 2, and 3 above).

In some embodiments, the terms of a general confidentially or nondisclosure agreement may be provided to the worker for acceptance. That is, because some or all of the projects registered by an employer may contain sensitive, confidential information, workers may be required to agree not to disclose to third parties any information obtained by virtue of their participation in work sessions. Thus, if an employer wishing to gauge consumer feedback about a new product packaging design were to register a survey featuring the new product design, workers employed to provide feedback about the design would be contractually bound to not disclose information about the design to third parties.

TABLE 3

| Task identifier | Project identifier | Employer identifier | Task description | Compensation | Performance conditions/ prequisites | Payment conditions |
|---|---|---|---|---|---|---|
| 321321 | 55555 | 190357 | Survey question at C://tasks.questions.55555.0001 | $.02 | None | Check only; once more than $5 has been earned |
| 321322 | 55555 | 190357 | Survey question at C://tasks.questions.55555.0002 | $.02 | None | Check only; once more than $5 has been earned |

Step 3: Determine Whether Potential Worker is Permitted to Participate in Work Sessions Based on Stored Rules.

After the worker provides the necessary registration data to the central computer, the central computer consults stored rules (e.g., in a database) to determine whether or not the worker meets the general requirements necessary to participate in work sessions.

For example, the central computer may refuse to register any potential worker who does not accept the terms of a nondisclosure agreement.

Or, the central computer may refuse to register any potential worker who does not reside within a certain geographical region. For example, a stored rule may indicate that workers must be citizens of the United States, as indicated through the provision of a valid SSN. In this case, the central server may receive a nine-digit number from the remote potential worker, and consult a remote database to determine whether or not the number corresponds to a validly issued SSN.

Further still, the central computer may refuse to register any potential worker under a certain age, as indicated by a database lookup based on a provided SSN. Such an embodiment may be desirable where local child labor laws limit work by individuals under certain ages. The central computer may optionally be configured to access a local or remote database comprised of such jurisdictional age limits. The central computer could consult the database so that the appropriate age limit is retrieved which corresponds to the potential worker's place of domicile. An example of such a database is shown in Table 4 below:

TABLE 4

| State | Minimum working age |
|---|---|
| NY | 16 |
| LA | 15 |
| IL | 17 |

Also, the central computer may refuse to register any potential worker who does not provide certain information by, for example, populating certain fillable fields of a Web page. For example, state and federal equal opportunity and/or labor laws and regulations may require the operator of the central computer to record the age, race and gender/sex of each potential worker, in which case any potential workers failing to provide such information may be returned to a previous step in the process (e.g., so that the required information can be provided), or the session may end.

Furthermore, in some embodiments, stored rules may require that the user meet certain minimum hardware requirements. That is, the system may require that user devices be capable of a certain minimum amount of functionality. For example, the system may require that a user device be configured to communicate with the central computer through a modem of a certain speed, that the user device comprise a processor of a certain speed, etc.

Step 4: Create Record for Worker in Worker Database.

A record for the worker is created in a worker database including at least some of the received registration data. According to some embodiments, a worker identification number may be assigned to the worker and stored in the worker's record. The worker database may be read from and/or written to by the central computer during the below-described work session process.

An exemplary worker database is shown in Table 5 below:

TABLE 5

| Worker identifier | Worker password | Worker name | Worker address | Worker email address | Desired form of payment/ Worker financial account number | Complete, uncompensated tasks | Total compensation due | Total hours worked within last 24 hours | Total hours worked within last 30 days |
|---|---|---|---|---|---|---|---|---|---|
| 222 | Fish | Bill Jones | 2 Main Street, Town, NY, USA | bjones@emailsite.com | Check | Task identifiers: 321321, 321322 | $.04 | .00146 | .00146 |

Work Sessions

Step 1: Receive Request to Initiate Work Session.

Registered workers can initiate work sessions without having previously scheduled a work session. Such flexibility allows registered workers to log on at any time and earn money by performing micro-tasks.

The request to initiate a work session can be communicated by the worker in many ways, including but not limited to (1) using a mouse or other device peripheral to the user computer to click on an area of a graphical user interface, such as a Web page, hosed by the central computer, or (2) using a handheld wireless device such as a cellular telephone to transmit dual-tone multi-frequency (DTMF) tones to an Interactive Voice Response Unit (IVRU) operatively connected to the central computer.

In some embodiments, the central computer may at this point request and/or receive a worker identifier and/or password for security purposes.

Step 2: Determine If Request to Initiate Work Session is Valid.

The central computer then determines if the received request to initiate a work session is valid. In some embodiments, the central computer may validate the request by simply checking the received worker identifier and/or password against the worker database to determine if they correspond to a valid record.

Further, in some embodiments, the central computer may validate the request to initiate a work session by determining whether or not the worker is attempting to initiate a work session from an unauthorized location or using unauthorized equipment. For example, various employers may wish to prevent their employees from performing tasks for other employers (by participating in work sessions) during regular working hours. As such, an employer may register with the central computer so that workers cannot participate in work sessions using company computers. Thus, an employer may register the IP addresses or machine identifiers of personal computers in its corporate network. Upon receiving a request to initiate a work session, the central computer may then consult a database comprised of such identification information to determine whether or not the worker is attempting to initiate a work session from an unauthorized location or machine. If so, the central computer may determine that the request to initiate the work session is invalid, and may terminate the process at this point. An exemplary database comprising prohibited employer devices is shown in Table 6 below:

TABLE 6

| Employer | Device identifier | Work session participation rule(s) |
| --- | --- | --- |
| ABC Corporation | 1234.1234.1234.1234 | Not to be used in work sessions |
| ABC Corporation | 1234.1234.1234.1235 | Not to be used in work sessions |
| XYZ Ltd. | 4321.4321.4321.4321 | Not to be used in work sessions between 8AM and 6PM EST. |

In some embodiments, the step of validating a request to initiate a work session may include the step of determining whether or not a given worker has surpassed a given work limit or compensation limit. The operator of the central controller may wish to limit the amount of work that can be done within a certain period of time in order to comply with federal or state labor laws or regulations. For example, a given law may dictate that workers in the relevant jurisdiction may not work for more than 16 hours per day. In this case, the central computer would consult a worker's record in the worker database and determine if the worker has performed more than 16 hours of work within the last 24 hours, and if so, the central computer may determine that the request to initiate the work session is invalid, and may terminate the process at this point. It should be noted that such a time limit may also be desirable in settings where the operator of the central controller wishes to preserve the independent contractor status of workers by limiting the amount of hours available to workers.

Alternatively or additionally, the operator of the central controller may wish to limit the amount of compensation that can be earned by a given worker in a certain period of time. In this case, the central computer may be configured to access a database that stores rules governing compensation limits, and may consult such a database and the worker database to determine if a given worker has surpassed a compensation limit. If so, the central computer may determine that the request to initiate the work session is invalid, and may terminate the process at this point.

Step 3: Identify Task in Task Database.

Once a request to initiate a work session is validated, the central computer identifies a task in a task database.

According to some embodiments, the central computer allocates a task to a worker by simply, in a serial fashion, selecting the next available task from the task database.

According to other embodiments, the central computer allocates tasks to a worker according to task performance conditions or prerequisites that are stored in a task database. Thus, the central computer may serially review records in a task database, searching for tasks for which the worker may be suitable.

For example, a rule may dictate that only workers from a certain geographical area may be routed a particular task. Alternatively or additionally, a rule may dictate that workers are not to receive tasks that they have already performed (e.g., so that a worker does not get asked the same survey question twice).

Step 4: Transmit Task Data to Worker Including Task Content and Response Options.

Once it is determined which task a worker will be routed, task data is transmitted to the worker device. In some embodiments, the data that may be transmitted may include a textual description of the task and a plurality of response options (e.g., a question and several possible answers, such as "yes" or "no", or several multiple choice answers). Further, the task data may include digital files comprising images or sounds.

An enumerated list of several different types of tasks that may be registered by employers and performed workers is provided below (see section below entitled "Application Contexts").

Step 5: Receive Selected Response(s) from Worker.

After the worker receives the task data, the worker performs the task and sends the central computer his or her response using the worker device. For example, after reading a question and reviewing the possible answer choices, a user may press a key on a worker device corresponding to a particular answer choice, and thereby transmit the selected answer choice to the central computer.

Step 6: Evaluate Received Response(s) and Process Accordingly.

According to some embodiments, a fraud-detection subroutine may be executed at this point to ensure that the worker is actually making a bona fide effort to contemplate tasks and transmit thoughtful responses. That is, the system may evaluate received responses against a database of stored rules to ensure that the worker is not merely providing a repetitive, thoughtless set of responses (e.g., answering every question with a "yes" response). Several methods for ensuring worker attentiveness are disclosed more fully with reference to U.S. Pat. No. 6,093,026 entitled METHOD AND APPARATUS FOR ADMINISTERING A SURVEY, issued Jul. 25, 2000, the entirety of which is incorporated by reference herein for all purposes.

Step 7: Adjust Worker Rating Based on Evaluation of Received Response(s).

In embodiments implementing fraud-detection methodology, a worker rating may be adjusted to reflect the worker's attentiveness and care in answering questions. Systems and methods for updating a worker rating based on a user's degree of attentiveness are described with reference to U.S. Pat. No. 6,093,026.

Step 8: Determine If a Session Termination Rule is Met. If not, Return to Step 3. If So, Proceed to Step 9.

Next, the central computer determines if a stored session termination rule is met. If a session termination rule is met, the process continues to Step 9. If not, the process returns to Step 3, where the worker would continue participating in the work session.

In one embodiment, the central computer makes this determination periodically. In another embodiment, the central computer makes this determination continuously or substantially continuously. Further, according to some embodiments, the central computer makes this determination in response to a worker request. That is, in some embodiments, a worker may unilaterally end his or her participation in a work session by transmitting to the central server a signal indicating the desire to do so. The ability to terminate work sessions unilaterally adds flexibility to work sessions, and allows for the performance of micro-tasks at traditionally unconventional times.

In some embodiments, session termination rules may constitute time limits for work sessions to ensure that a worker does not work for more than a certain amount of time within a certain period. Such rules may be desirable in contexts that do not permit continuous work for a certain period without a break. For example, laws, regulations, and/or labor contracts may dictate that a break must be given for every 8 hours of work. Or, as workers may be performing micro-tasks by operating worker devices such as personal computers, concerns about eye-strain, carpel tunnel syndrome, or other types of fatigue may necessitate a session termination rule that ends sessions after a predefined amount of time. Such rules would force a break in the continuity of a work session once the time limit has been reached. Further, session termination rules may dictate that sessions terminate once workers demonstrate a marked change (i.e., deterioration) in performance. For example, if a worker's average response time (the time between the transmission of task data and the receipt of a response) increases beyond a certain threshold during a work session, a session termination rule may be triggered. Or, if a worker's provided responses indicate a lack of attentiveness as discussed with reference to U.S. Pat. No. 6,093,026, a session termination rule may be triggered.

Alternatively or additionally, session termination rules may constitute compensation limits to ensure that a worker does not earn more than a certain amount of compensation within a certain period. For example, once a worker has earned enough to pay for a currently outstanding service bill (e.g., a bill for cable or ISP services), a session may terminate. Such a rule would be desirable where the operator of the central service does not wish to compensate workers in cash, but would rather limit compensation to an offsetting of an outstanding bill for services.

Step 9: Calculate and Initiate Provision of Compensation to Worker Based on Session Data.

Timing:

After a work session, the central computer system may determine the amount of compensation due to a worker and initiate the provision of compensation. In some embodiments, this step is initiated immediately following the termination of a work session. In other embodiments, the calculation and provision of compensation is done periodically (e.g., weekly, monthly; at the end of a billing cycle). Further, in some embodiments, the calculation and provision of compensation could be performed by the central computer upon the worker's request (e.g., when a worker logs on and clicks a button to request payment to his financial account on file with the central computer).

In some embodiments, payment may be withheld at this step if the transaction costs of providing compensation are not justified by the amount of payment. That is, because the present invention facilitates individually compensable micro-tasks, it may be desirable to have a determination of when is most cost-effective to remit payment. For example, because it likely costs at least $0.50 to process a credit to a credit card account, payment for micro-tasks may be withheld until there is at least $0.60 of work performed by a given worker. An exemplary database follows that stores rules that may be used in determining when compensation due a worker sufficiently outweighs the transaction costs of a particular form of payment:

TABLE 7

| Form of payment | Transaction cost | Required compensation due to justify payment |
|---|---|---|
| Credit card | $ .50 | $ .75 |
| PayPal ® | $ .02 | $ .25 |
| Check | $1.50 | $1.55 |
| Credit to ISP service account | $ .00 | $ .01 |

Calculation of Payment Amount:

In some embodiments, the central computer calculates pay rates based on an advertised per-task rate. For example, if a worker performed 10 tasks priced at $0.10 each, the worker would have earned $1. Further, in some embodiments, workers may be compensated at different pay rates according to their rating status. For example, workers rated at "5" may receive a rate of $0.02/question, while workers rated at "4" may receive a rate of $0.01/question. In such an embodiment, the central computer would multiply the number of questions answered by the given worker's pay rate.

Further, the step of calculating a payment amount may also include an accounting for miscellaneous fees and charges. For example, the central computer may reduce gross compensation due by various amounts including, for example: (1) state and federal tax withholding amounts, (2) insurance premiums or co-pays, and/or (3) past due or penalty amounts associated with a service account (e.g., ISP or cellular phone service accounts).

Further still, the step of calculating a payment amount may also include a credit for a "bonus" once a threshold amount of work has been performed (e.g., every year, every X hours of work performed, etc.).

It should be noted that, in some embodiments, the step of calculating the payment amount may take place before the optional step of determining whether or not the transaction costs associated with the particular form of payment are justified by the amount of payment due.

Payment Mechanisms:

In some embodiments, after calculating the amount of payment due, the central computer may initiate payment by instructing that an account associated with the worker be credited. More particularly, in some embodiments, the central computer may communicate with a remote server owned by a financial institution, and may indicate an authorization to charge an account associated with the owner of the central computer and credit an account associated with the worker.

In other embodiments, the central computer would initiate payment by crediting a service account associated with the worker. For example, where the central computer is operated by a provider of a service, such as an Internet Service Provider, a cable TV service provider or a cellular telephone service provider, a worker's service account may be offset by any earned compensation. Thus, in such embodiments, workers may offset their service bills by performing micro-tasks. However, such service providers may optionally limit the ability to earn compensation by providing that workers can only earn up to the amount owed to the service provider. Should workers earn less than is currently owed to the service provider, the central computer may output a bill for the difference between the value of the services rendered and the amount of compensation due. Further, in some embodiments, workers may earn more compensation than they currently owe for services, and the difference can be credited to a future billing cycle.

Form of Payment:

Many different forms or mediums of payment are contemplated. As discussed above, the central computer could credit to a financial account associated with the worker, including service accounts, credit accounts, checking accounts, and the like. Alternatively, the central computer may authorize the provision of other forms of compensation.

For example, product manufacturers may "employ" customers of their products and compensate them with rebates. In other words, customers may "earn" a rebate or coupon by answering questions about a previously-purchased product, providing feedback and the like. Aside from potentially collecting valuable consumer feedback and data, such a program may simply be a way to interact with a customer after a purchase, enhancing the customer's image of the product.

Alternatively, in another embodiment, workers may be compensated with discounts on merchandise they have not yet purchased. In addition to serving as a vehicle for providing interested customers with discounts, such an embodiment would be a useful way to identify price-sensitive customers.

In another alternate embodiment, workers may be allowed to view premium content (e.g., sports games, concerts) for "free" if they perform micro-tasks. For example, in an embodiment where a worker initiates a work session by logging on to the central computer through his personal computer, the worker may earn passwords or codes that allow the worker to view a premium sports event on a restricted-access website.

Further, in another embodiment, workers may be allowed to earn event tickets (e.g., tickets to concerts, sporting events) or travel vouchers (e.g., airline tickets).

Step 10: Aggregate and Transmit Responses to Employing Party.

Periodically or at the end of a project (i.e., once all the tasks associated with a single, common project are completed), the central system would transmit all received responses associated with the project (potentially from many workers) to the employing party.

In one embodiment, the central system merely transmits the raw response data. In another embodiment, the central system could process the responses by preparing summaries, statistics, charts, graphs, or the like based on the received responses. The operator of the central controller may optionally charge a fee to the employing party for such additional processing.

Step 11: Charge Employer for Work Allocation Service.

The central computer may then charge the employer for the services performed by the remote workers. For example, the central computer may initiate a billing routine or charge a predetermined financial account associated with the employer. The amount charged to the employer may reflect (1) an amount of work performed by, or compensation paid to, workers and/or (2) a service fee.

Application Contexts

Many different types of tasks can be registered by employers and performed by workers. Generally, low-skill tasks that can be performed in conjunction with the present invention constitute tasks whereby a worker must receive task data and select a response from a limited set of responses. For example, low-skill tasks used in the present invention may require workers to make "binary" (i.e., "yes" or "no") decisions, or to select from an otherwise limited set of possible responses (e.g., multiple choice answers). A list of various exemplary applications of the present invention follow.

1. Opinion Polls and Research.

a. Product packaging. In some embodiments, consumer products manufacturers, such as Proctor & Gamble, may employ workers to provide their opinion as to product packaging (e.g., "Which packaging do you like better, A or B?").

b. Product rating/rescreening. In some embodiments, workers may be asked simple binary (i.e., "yes or no", "like or dislike") questions about their feelings toward certain products. For example, workers could quickly rate greeting cards ("insincere?" . . . "offensive?" . . . "pushy?").

c. Advertisement/commercial rating. In some embodiments, workers may be asked to rate which of two advertisements or commercials they like better.

d. Broadcast media rating/feedback. Similarly, in some embodiments, workers may be asked to rate TV pilot programs or provide input that may be useful in making programming decisions ("like or dislike?", "which program would you watch if they were on at the same time, A or B?").

e. Product configuration. In some embodiments, workers could rate comparative options for how products are best configured. For example, large restaurant chains could employ workers to help identify which food items are best served together. Likewise, quick service restaurants could employ workers to define what constitutes a valuable "value meal", since consumer perceptions of value constantly change, especially in light of competition.

f. Product placement. In some embodiments, workers may provide feedback as to the proposed placement of items in retail stores or in advertisements. E.g., a worker may be asked to select from a plurality of images the setting in which the Coke bottle first became apparent to them.

g. Public Relations: word, phrase or speech rating. Similarly, in some embodiments, corporations, politicians and other public figures may use the present invention to test for negative/positive connotations and effects of words, phrases, or speeches. E.g., a question may ask: "Which phrase do you prefer: (A) "tax refund" or (2) "tax rebate?"

h. Simple, ad hoc surveys. In some embodiments, an employer can use the inventive system to administer quick surveys about any topic, provided that the responses are limited to simple selection of relatively few possibilities. For example, a lifestyle-oriented magazine may utilize the system to conduct a "hot or not?" survey. Or, news organizations may use the system to broaden the base of potential respondents on particular survey questions.

i. Lie detection. In some embodiments workers could watch testimony, speeches or the like and decide whether or not someone is "lying" or "telling the truth". For example, trial lawyers may wish to use the inventive system to see how a mock jury would react to a potential witness. Likewise, politicians may test the sentiment of the voting populous or a relevant constituency as to his or her stated version of a particular newsworthy issue/scandal.

j. Appearance evaluation. In some embodiments, employers may post images for review by workers. Thus, a lawyer may post two digital images of a potential witness (e.g., a criminal defendant) wearing different outfits, hairstyles, etc. Workers may then earn compensation by providing their opinion as to which of the two makes the potential witness appear more credible.

2. Quality Control. In some embodiments, businesses may utilize the inventive system to ensure quality of their products.

a. Manufacturing. In some embodiments, workers can be employed to monitor images of assembly-line instances for early problem detection, potentially saving manufacturers from downstream costs associated with remedying problems. For example, a monitoring device such as a digital video camera, in conjunction with image-analysis software, may be employed to scan the mundane operation of an assembly line and route images of nonconforming events (i.e., images of product line instances that do not conform to a reference image) to workers for evaluation. Alternatively, workers may simply watch feeds or images of the assembly line themselves, reporting nonconforming/problem units as they are generated.

b. Package assembly. In some embodiments, workers may monitor images captured by monitoring devices at warehouse operations to ensure that packages contain all invoiced items before they are shipped. For example, for each box of items to be shipped, an image could be captured (e.g., a top view of the box so as to make the boxes' contents apparent). Both the image and a list of invoiced items could be transmitted to a worker. The list of items and the image may appear on the worker's screen, and the worker could simply check off each item on the list if it is included in the box.

c. Cleanliness. Employers may utilize the present invention to monitor the cleanliness of physical settings such as businesses, parks, etc. Thus, in some embodiments, workers could monitor images taken from monitoring devices at restaurants and kitchens to verify that kitchens are clean, that food is prepared in a healthy, clean manner, and the like by watching the preparation process and reporting potential problems (e.g., by reporting "clean" or "unsanitary").

3. Support for Artificial Intelligence Systems. Although artificial intelligence is increasingly used in daily life, a major problem preventing further utilization is its accuracy. Thus, in some embodiments, the present invention could be used to bolster the accuracy of such systems. In other words, workers could provide back-up support and error-checking for most any artificial intelligence system. For example:

a. Assistance with speech and handwriting recognition. Currently, prior art speech-to-text conversion software is, at best, 95% accurate. Prior art handwriting recognition software is similarly inaccurate. Thus, in some embodiments of the present invention, executives, lawyers and others using speech and handwriting recognition could utilize the inventive system to have documents checked for accuracy. Simply, workers could just respond to different portions of text by informing the system if there is an "error" or "no error". In one such embodiment, workers could compare text to supposedly-corresponding voice files and indicate "match" or "no match". In an alternate embodiment, workers could just read portions of text and answer "correct" or "error".

b. Detection of unusual account activity. Currently, financial institutions employ algorithms to determine whether or not account activity is unusual. However, detected activity is often not representative of a security problem (e.g., when a cardholder is on vacation, an account may be inappropriately disabled merely due to a large volume of purchases), and conversely, fraudulent activity often goes undetected. Thus, in some embodiments, transaction data is parsed and redacted to ensure anonymity (e.g., separated from account numbers), and sent to workers to verify normality/abnormality of transaction patterns. Workers could respond by confirming whether or not a transaction pattern is "normal" or "abnormal".

c. Automated customer service. The present invention may be used to confirm the appropriateness/accuracy of automated customer service responses. For example, where software is employed to scan customer emails and provide responses based on keywords therein, workers could read the proposed responses before they are sent to customers, and thereby confirm whether or not proposed automated responses squarely address the corresponding customer issues.

4. Retail Assistance. Generally, retailers may use the inventive system to:

a. Spot undetected customer issues.

i. Customer dissatisfaction/satisfaction. In some embodiments, workers can view images of retail customers to determine if they are satisfied or dissatisfied with services. This information can be useful in determining how to allocate customer service representatives, and where to focus business resources generally. Such an embodiment is desirable because customer satisfaction often can be determined based on nonverbal signals, which are best detected and interpreted by human monitors (e.g., facial expressions, body movements).

b. Spot undetected employee issues assist with HR functions.

i. Poor service. In some embodiments, workers can be employed to (1) view images taken from monitoring devices of retail employees as they serve customers and (2) report bad service. Also, workers can be employed to monitor when customers are not getting served. For example, a worker might simply click a button on a user device when a given customer "needs service", such as when a customer appears confused, when they have been wandering the store, when they have been looking at a store directory or map, when they have been reading a product label for a long period of time, etc.

ii. Employee theft. In some embodiments, workers can be employed to view images, taken from monitoring devices, of retail clerks as they operate cash registers or otherwise handle employer assets. Workers could report "theft" or "OK" for each transaction, and could thereby perform a very useful function in detecting fraud or theft (e.g., "skimming" of the cash register).

iii. Employee rating. In some embodiments, consumers employed as workers could simply watch images of employees and rate them as "good" or "bad" and/or provide simple feedback inputs as "fire," "retrain," or "promote".

c. Spot undetected operational issues and assist routine operations.

i. Inventory monitoring. In some embodiments, workers may view images of a retailer's shelves, and report "sufficient inventory" or "out of stock".

ii. Age/ID Verification. In some embodiments, workers may be transmitted camera images taken from already-in-place security cameras at convenience stores and simply determine whether each customer "looks" a certain age or not. Further, in such embodiments, the capture and transmission of images may be limited to when certain products are purchased (tobacco or alcohol), as indicated by products' UPC codes. Thus, a worker could simply provide "over the shoulder" validation for a merchant's decision to sell an individual cigarettes by selecting either "at least 18" or "under 18" after viewing the individual's image. Similarly, workers could view entrances (e.g., gates, doors) of certain age-restricted venues such as bars, events, etc.

5. Environmental Monitoring. In some embodiments, governmental or not-for-profit groups may employ workers to monitor images to determine environmental and agricultural problems as they develop. For example, workers could compare images taken every two weeks to determine if a given crop appears to be diseased, or if a given natural resource is deteriorating.

6. Municipal/Local Law Enforcement. In some embodiments, municipalities and local law enforcement agencies may employ workers to view images taken from remote monitoring devices and review such images:

a. Public areas. Parks and other public areas (e.g., street corners) may be monitored for suspicious activity. Simply, workers could simply view images and report "no problem" or "problem."

b. Parking. Workers could act as remote "meter maids" by viewing images of parking spots and indicating whether there is a "violation" or "no violation."

c. Moving violations. Workers could view images of intersections and confirm moving violations (e.g., if a car ran a red light).

7. The Internet. The following embodiments may be particularly attractive to an Internet Service Provider who owns and operates the central computer.

a. Development of the World Wide Web, or certain "communities" therein.

i. Rating of Websites. In some embodiments, workers who are customers of an ISP rate websites by clicking a button on a graphical user interface (e.g., a browser) indicative of a selected rating. Workers could rate sites quickly for general quality/appeal (e.g., one to five "stars"), for age-appropriateness (e.g., PG, R, X; or just "child safe" or "adults only"), etc. The ISP's central computer could, in turn, average received ratings and publish them for customers to see (e.g., "This site's average user rating is 3.")

ii. Categorizing web sites. In some embodiments, workers may be charged with the task of viewing a web site and selecting an appropriate category label (e.g., news, arts, special categories). Then, within categories, workers could subcategorize to add further specificity (e.g., Connecticut news, national news, etc.). Ultimately, the central computer could use such "metadata" in performing Web searching and navigation (i.e., in determining relevant search results).

iii. Linking of web sites. In some embodiments, the central computer (e.g., ISP server) can present workers with two websites (e.g., in separate sub-windows), and workers can determine whether or not the two sites should be linked together by hyperlinks. Automatic selection of the two sites can be done randomly or quasi-intelligently (e.g., keyword-based).

b. Content previewing. In some embodiments, subscribers to an ISP service may pay a premium to employ a worker to make sure that minors (subscribers' sons and daughters) are not viewing inappropriate content, communicating with potentially threatening individuals, etc. In such an embodiment, workers could be routed Web pages, search results, or messages before a minor receives such content. The worker could be asked whether not such content is "appropriate" or "inappropriate" for a minor. If the content is appropriate, it could be transmitted to the minor. If the content is deemed inappropriate, the content would not be transmitted to the minor.

c. Human "Spam" filters. In some embodiments, as a premium service to ISP subscribers, workers may be employed to view email messages that initially appear to be unsolicited ("Spam") based on stored rules (e.g., if thousands of similar emails are simultaneously sent to other recipients from a single address). Such messages that appear to be spam could be deleted, marked, or sorted into a separate mailbox by workers. To ensure privacy, email addresses, names, addresses, phone numbers and other identifying information could be automatically redacted from messages.

8. Social.

a. Dating/matching assistance. In some embodiments, workers may rate potentially compatible dating candidates by viewing two pictures and/or textual profiles and selecting "compatible" or "not compatible."

9. Education.

a. Grading papers. In some embodiments, workers may log on and correct papers or tests (e.g., spelling tests, multiple choice tests, etc.).

Additional Embodiments

In some embodiments, workers may perform micro-tasks from their telephones while "on hold". For example, Tim Smith, a Verizon customer, calls a customer service number for a computer problem he is having. While waiting on hold, Tim presses #123, which triggers an option that lets him earn money while he is on hold. While he is on hold, Tim proceeds to answer questions, and thereby earn compensation. However, his work session is terminated when a customer service representative picks up. Various embodiments for managing consumer-to-consumer customer service while a first customer is waiting himself for customer service is discussed more fully with reference to Applicant's U.S. Pat. No. 5,978,467, entitled METHOD AND APPARATUS FOR ENABLING INTERACTION BETWEEN CALLERS WITH CALLS POSITIONED IN A QUEUE, issued Nov. 2, 1999, and U.S. Pat. No. 6,125,178, entitled METHOD AND APPARATUS FOR ENABLING INTERACTION BETWEEN CALLERS WITH CALLS POSITIONED IN A QUEUE, issued Sep. 26, 2000, the entirety of which is incorporated by reference herein for all purposes.

In some embodiments, individual users may post tasks to be performed by peers. That is, commercial or associational employers are not necessarily the only types of employers that can benefit from the present invention. Thus, an individual may seek a short answer to a particular question from an individual having similar demographic characteristics. For example, a high school student may wish to ask any other high school age student what is a good movie to take a date to on the upcoming weekend, and may indicate that she will pay $0.25 for the answer. Thus, any high school student could respond with the answer (e.g., via a peer-to-peer communications system such as AOL's Instant Messenger) and thereby earn the offered compensation.

The following definitions are used herein below, unless otherwise indicated.

Monitoring apparatus, monitoring device—A device capable of receiving, via an input device, a signal and outputting the signal to a central computer and/or a user computer. In some embodiments, a monitoring apparatus may include (i) a processor, such as one based on the Intel® Pentium® series processor, and/or (ii) a data storage device/memory. Example monitoring devices include those that are capable of converting analog signals into digital data files. Such devices include, but are not limited to: (a) digital video cameras, (b) digital video cameras equipped with motion detection and/or "short loop" tripping features, and (c) digital cameras.

Monitoring party, patroller, spotter, user, viewer—A person who participates in the remote monitoring of sites, typically in exchange for compensation. In some embodiments, such persons are members of the public that have no prior affiliation with monitored sites. Thus, according to some embodiments, images and/or other data that is sent to such viewers for review is selected randomly or substantially randomly, and/or may be edited (e.g., redacted) so that such viewers cannot determine the identity and whereabouts of particular sites. In this manner, the inventive system provides a secure method and system for allowing members of the public to, in an ad hoc manner, earn compensation for monitoring the security of private property.

"No-man" zone—A security-sensitive area on a monitored site where no humans or vehicles should be monitored (e.g., no humans should be present).

Site, remote site, property—Property, including but not limited to real property, which is to be monitored. Such property is monitored by at least one monitoring apparatus.

Supervisor, trained professional, professional—An employee or agent of the central computer's owner (e.g., Net Patrol). In some embodiments, supervisors assist site owners in configuring and initializing monitoring devices.

User computer, user device, device—A device capable of (i) receiving a signal from a central computer and/or a monitoring apparatus, (ii) outputting a signal to a user (i.e., a viewer), (iii) receiving a response from a user via an input device, and (iv) transmitting a signal indicative of the response to a central computer and/or a monitoring apparatus. In some embodiments, a user device may include (1) a processor, such as one based on the Intel® Pentium® series processor, and/or (2) a data storage device/memory. Example user devices include personal computers and cellular telephones.

A. System Configuration

1. Network Embodiments

The embodiments described below can be configured to work in a network environment whereby a central computer, a user (e.g., viewer) computer and/or the monitoring device communicate with each other directly or indirectly, via a wired or wireless medium such as the Internet, LAN, WAN or Ethernet, Token Ring, or via any appropriate communications means or combination of communications means. Communication between the devices and computers, and among the devices, may be direct or indirect, such as over the Internet through a Website maintained by a computer on a remote server or over an on-line data network including commercial on-line service providers, bulletin board systems and the like. In yet other embodiments, the devices may communicate with one another and/or a computer over RF, cable TV, satellite links and the like.

Some, but not all, possible communication networks that may comprise the network or be otherwise part of the system include: a local area network (LAN), a wide area network (WAN), the Internet, a telephone line, a cable line, a radio channel, an optical communications line, and a satellite communications link. Possible communications protocols that may be part of the system include: Ethernet (or IEEE 802.3), SAP, ATP, Bluetooth™, and TCP/IP. Further, networking of devices and computers may include use of 802.11b and related wireless protocols and/or use of cell networks (GSM and other emerging standards).

Those skilled in the art will understand that computers and devices in communication with each other need not be continually transmitting to each other. On the contrary, such computers and devices need only transmit to each other as necessary, and may actually refrain from exchanging data most of the time. For example, a device in communication with another device via the Internet may not transmit data to the other device for weeks at a time.

In an embodiment, a central computer may not be necessary and/or preferred. For example, the present invention may, in one or more embodiments, be practiced on a monitoring device in communication only with one or more user computers. In such an embodiment, any functions described as performed by the central computer or data described as stored on the central computer may instead be performed by or stored on one or more monitoring devices or user computers.

2. Network Security

Communication among computers and devices may be encrypted to ensure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc., 2d ed., 1996.

3. Data Storage Devices/Memory

For each computer and/or device (i.e., the central computer, the user computer, and/or the monitoring apparatus), a processor may be in communication with a memory and a communications port (e.g., for communicating with one or more other computers or devices). The memory may comprise an appropriate combination of magnetic, optical and/or semiconductor memory, and may include, for example, Random Access Memory (RAM), Read-Only Memory (ROM), a compact disc and/or a hard disk. The memory may comprise or include any type of computer-readable medium. The processor and the memory may each be, for example: (i) located entirely within a single computer or other device; or (ii) connected to each other by a remote communication medium, such as a serial port cable, telephone line or radio frequency transceiver.

In one, several or all computers or devices, a memory may store a program for controlling a processor. The processor performs instructions of the program, and thereby operates in accordance with the present invention, and particularly in accordance with the methods described in detail herein. The program may be stored in a compressed, uncompiled and/or encrypted format. The program furthermore includes program elements that may be necessary, such as an operating system, a database management system and "device drivers" for allowing the processor to interface with computer peripheral devices. Appropriate program elements are known to those skilled in the art, and need not be described in detail herein.

The term "computer-readable medium" as used herein refers to any medium that participates in providing instructions to a processor for execution. Such a medium may take many forms, including but not limited to, non-volatile media, volatile media, and transmission media. Non-volatile media include, for example, optical or magnetic disks, such as memory. Volatile media include dynamic random access memory (DRAM), which typically constitutes the main memory. Transmission media include coaxial cables, copper wire and fiber optics, including the wires that comprise a system bus coupled to the processor. Transmission media may carry acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying one or more sequences of one or more instructions to a processor for execution. For example, the instructions may initially be borne on a magnetic disk of a remote computer. The remote computer can load the instructions into its dynamic memory and send the instructions over a telephone line using a modem. A modem local to a particular computer or device can receive the data on the telephone line and use an infrared transmitter to convert the data to an infrared signal. An infrared detector can receive the data carried in the infrared signal and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of carrier waves that carry data streams representing various types of information. Thus, a computer or device may obtain instructions in the form of a carrier wave.

According to an embodiment of the present invention, the instructions of the program may be read into a main memory from another computer-readable medium, such from a ROM. The execution of sequences of the instructions in a program causes the processor perform the process steps described herein. In alternate embodiments, hard-wired circuitry may be used in place of, or in combination with, software instructions for implementation of the processes of the present invention. Thus, embodiments of the present invention are not limited to any specific combination of hardware and software.

The memory also may store a plurality of databases. Some or all of the data stored in each database may be described herein. Any described entries of the databases represent exemplary information only; those skilled in the art will understand that the number and content of the entries can be different from those illustrated herein. Further, despite any description of the databases as tabular, relational databases, an object-based model could be used to store and manipulate the data types of the present invention and likewise, object methods or behaviors can be used to implement the processes of the present invention.

B. Processes

1. Site Registration

Site owners and/or operators may initially register with the system in order have their sites monitored by viewers. It is contemplated that site owners will purchase camera and/or other monitoring device equipment from the operator of the central computer (e.g., Net Patrol), although it is possible that site owners may register other existing cameras and/or other monitoring devices with the central computer.

In embodiments where monitoring devices comprise cameras such as video cameras, cameras and supporting peripheral hardware may have embedded computer devices and may support various standard internetworking and operating system protocols (e.g., embedded Linux chips that support HTTP, SSL, FTP, CGI, Java, etc.). For example, cameras available from Axis® Communications, Inc. may be employed, including model 2420 series network cameras with infrared (IR) lenses, model 250-S MPEG-2 network video servers, and model 2191 audio modules. Infrared lenses may be desirable for low-light (i.e., nighttime) image capture.

In some embodiments, cameras may also be equipped with PTZ (Pan/Tilt/Zoom) mechanisms to facilitate remote adjustment of field of view, focus, and the like. Further, in some embodiments, cameras may be configured to support on-demand requests for static and motion images submitted by remote parties, such as site owners, viewers and supervisors.

It may also be desirable that cameras are weather-insulated as they may be located outdoors and subjected to extreme temperatures, wind and precipitation. Further, each camera preferably may have two independent circuits, so that if one fails the other can serve as a back-up. Similarly, cameras may employ dual, redundant power sources, such that if one power source is unavailable, a back-up power source (e.g., batteries, generators, etc.) may be used. Indeed, in some embodiments, completely autonomous, free-standing image capture hardware may be employed. Such hardware may use solar panels and high capacity energy cells for power, and may use cellular/satellite communications for networking.

In some embodiments, the inventive system will likely tie into/ride on existing alarm systems. In such embodiments, the camera hardware could be initially installed as part of the alarm system or could be subsequently added on as a retrofit. In either case, a user installation process may entail remote communication with a Net Patrol representative (e.g., a trained professional). Alternatively, the cameras may be installed professionally.

After the site owners obtain suitable monitoring devices, site owners may register with the system by interacting with the central computer in accordance with the following process steps.

b. Initial Customer Registration

In some embodiments, after cameras are installed, a registration process may follow. For example, cameras may be addressed (IP) and registered in database. Also, the central system may record the type of room (e.g., bedroom), the security priority assigned to the room (e.g., bedrooms are more important than kitchen), and the times the camera is to be active (e.g., only between 9 AM and 5 PM). Also, GPS coordinates may be registered so that the system can later determine if the camera has been moved or tampered with (e.g., the system may make periodic queries to monitoring devices, and/or any change in position may trigger a checkup process). Further, the system may require registration of the site's postal/street address, a geographically relevant emergency dispatch number (i.e., an emergency dispatch phone number corresponding to the site's local area), and the phone number of a relative of the site owner.

c. Testing

After cameras are installed, a test sequence may ensue to verify visibility and identify coverage gaps. For example, a site owner may be asked to walk through his or her house and a supervisor could verify coverage/identify gaps. The test may be recorded so that there is a record of the area that the supervisor and/or his or her employer (e.g., Net Patrol) is responsible for.

Also, there may be periodic, remote tests of the cameras to ensure that they are working properly. This could be done at non-invasive times, such as when a conventional alarm system is set and occupants have left the house. This would minimize any perceived privacy intrusion.

Further, testing may entail establishing a threshold for motion detection (e.g., for use in embodiments where image transmission is to be triggered upon motion detection). In this manner, the system can be programmed to ignore non-threatening motion, such as a small pet's movements at the site owner's premises.

2. "Patrol" Sessions/Service Administration a. Binary Determinations

In some embodiments, patrollers may log onto a central computer to monitor registered sites. In one embodiment, users are asked to make simple binary determinations about images received from monitored locations (e.g., "yes" or "no" answers). For example, in some embodiments, users may be asked to make a simple determination of whether or not they see a person in an image. That is, in private property contexts, there may be "no-man zones" at certain times (e.g., night) and in certain places (e.g., pools). Site owners may register, with the central computer, which areas (e.g., by camera location) are "no man" zones at particular times. For example, where a site owner has 3 cameras installed at a site, the site owner may indicate that "Camera Number 1", which happens to focus on the site owner's driveway, is a "no man" zone" between the hours of 10:30 PM and 5 AM.

Similarly, certain "buffer times" may be registered with the central computer, indicating the times during which activity at a site is to be disregarded. For example, the central computer may be programmed to disregard all images received when the site owner is enabling or disabling a conventional security/alarm system (e.g., within one minute from when a breach is first detected, thereby allowing the site owner one minute to provide the correct, disabling password or code).

Also, other helpful binary determinations may be made by viewers such as: (1) Are doors/windows open or closed? (2) Are the lights on or off? (3) Is the electricity on or off? (4) Does the address have phone service?

Indeed, the system can be configured to make binary determinations of seemingly non-binary questions simply by asking a binary question and verifying a first set of responses against subsequent verification sets (that may be more specific). For example, a first set of questions about an image taken at a private residence may ask: "Is this home safe or not safe?" Respondents may have a "hunch" that there is suspicious activity afoot at the site, and may respond by selecting the "not safe" option. Should a sufficient number of initial respondents similarly indicate "not safe", the system may (1) submit the same image/video clip to more users for verification, and/or (2) ask a more specific question ("Does it appear that the home is on fire? Yes or no?" Or, "Does it appear that an intruder is present in the home? Yes or no?").

b. Session Timing

In some embodiments, patrollers may be able to log on and log off of the central controller at any time (e.g., may start and stop monitoring sessions unilaterally at any time). However, cameras at a particular site may be only operative at certain times. For example, the camera system may turn on whenever the user turns on his or her alarm (or 30 seconds thereafter). Additionally or alternatively, the camera system may be triggered if a certain event occurs, such as if (1) security "hacks" or breaches are detected in related security systems (e.g., if the company's computer system is being hacked, the Net Patrol camera system may turn on), or (2) a noise/volume threshold is broken (e.g., by a scream or crash) as detected by a microphone.

3. Management of Patrollers a. Qualifying Patrollers

According to one embodiment, a process for qualifying patrollers (e.g., training and testing) is facilitated by the central computer. Training may comprise the communication of instructional information along with practice routines. Testing patrollers may entail testing the particular viewer(s) capabilities (e.g., attention level, vision, etc.) so that (1) those below a given threshold of attentiveness/responsiveness are banned from the system or retrained, and/or (2) content can be subsequently provided/transmitted in accordance with each patroller's individual level of attentiveness/responsiveness (e.g., higher contrast, higher resolution, more time on each image, etc.).

Further, qualifying patrollers may entail remote diagnostics of the patroller's computer (e.g., processor speed, connection speed, video card capability, screen resolution) so that the system can determine how to send images, which images to send, etc. (Alternatively, software to be downloaded from the central computer could have different settings for different hardware configurations.)

b. Session Initiation

In one embodiment, patrollers may simply log on to the central computer for each monitoring session by providing a username and password. More sophisticated embodiments may require coordination/attentiveness checks (e.g., trace a pattern with mouse cursor, view sequences of test images).

c. Motivators and Compensation i. Payment

In the simplest version, patrollers would be compensated in cash. Similarly, patrollers may be able to earn their way out of debt (credit cards, mortgages; banks could have borrowers monitor other mortgaged properties in the bank's portfolio).

ii. Game Themes, Prizes

Monitoring sessions could take the form of several games that can motivate and encourage patrollers to participate and pay attention. Such games may be comprised of the following characteristics and features:

Patrollers may be rated and rewarded based on performance (e.g., reporting of false positives).

Patrollers may be encouraged to pay attention by participating in a game that asks them to spot objects embedded in or superimposed on an image (e.g., spot and collect game pieces).

Homeowners and business owners (e.g., customers of Net Patrol) could post bounties as rewards for reporting certain events, behavior, etc.

In a "team play" embodiment, ad hoc groups may see the same image, and channel for discussion may open up (e.g., AOL Instant Messenger) so members can confer as to image content.

In a slot machine themed embodiment, the transmitted images can form the reels of slot machine. If the images are different, the patroller may win a prize. Such an embodiment would encourage patrollers to pay close attention to the content of the transmitted images.

d. Routing of Video Feeds and Images; Security Features

Video feeds and images may be routed to particular patrollers (1) randomly, (2) based on simple geographical constraints (e.g., different zip codes), (3) based on patroller history (e.g., never the same location twice), (4) based on customer (i.e., site owner) preferences (e.g., patrollers who are family members first; levels of expertise).

A related embodiment entails the editing/redacting of images and feeds to ensure anonymity for security and privacy purposes. For example, portions of an image may be blurred or otherwise concealed to protect sensitive aspects of the image.

e. Security Breach Procedures

Should a patroller detect a potential problem (e.g., a potential intruder), a process for managing and escalating the response would be triggered. For example, if the patroller detects a potential intruder, a two-way audio/video communication channel may open up between the patroller's user device and the monitoring device (or another device located at the monitored site) so that the patroller can initiate a "stand down" procedure, asking challenge/response questions (e.g., "what's the password?") to determine whether clearance should be granted or whether emergency sequences should be initiated. Emergency sequences can include simply allowing an alarm to be triggered or the direct dispatch of emergency responders.

Alternatively, such a "stand down" procedure can be facilitated/managed by the central computer system. For example, the central computer may transmit, to an output device at the site, a prompt for a password. The central computer may then receive a voice file from a person at the site (e.g., via a microphone), and interpret the content of the voice file using voice recognition software. The content of the voice file may then be compared to a stored password. Should the provided password be incorrect, or should no password be provided within a default time period, the central computer may initiate one or more emergency sequences, such as those described herein. It should be noted that such an automated stand down procedure may also be implemented in conjunction with the systems and methods disclosed above If a potential emergency is verified by a viewer and/or by the central computer pursuant to the above-described processes, images may be sent to a device of the site owner (e.g., a site owner's cellular phone, personal digital assistant, personal computer, television, etc.) for confirmation before a first responder is dispatched. In some embodiments, the site owner may confirm any potential problem by providing a response. For example, a site owner may receive an image on his cellular phone, and may be prompted to "press 1" if the person in the picture is not authorized to be at the premises. In this manner, by having the site owner involved in the monitoring session, false alarms may be reduced or virtually eliminated.

If a potential emergency is verified by a viewer and/or by the central computer and/or by the site owner, the images/feed may be made available to first responders (e.g., police, firemen, first aid workers, etc.) for assistance in dealing with the emergency. For example, responders may use the images/feed to determine where perpetrators are hiding in the house/business, where a fire is burning, whether anyone is left on a floor or in the building, etc. Similarly, as discussed more fully below, an audio communication channel may be opened to the occupants on the premises so that a customized, threat-specific evacuation plan can be communicated (e.g., "go out the back door") via a monitoring device or other device located at the site. Ultimately, the system may be used to prove the response activities of local responders (timing, procedures used, etc.).

f. Pricing

The site owner may pay for different degrees of service based on many metrics and service levels, including but not limited to, (1) artificial intelligence (AI) based prescreening sensitivity, (2) the number of cameras, (3) the frequency of image transmission, (4) the number of images that are transmitted, (5) the number of images that are transmitted until a site owner responds, (6) the number of patrollers, and (7) session times (e.g., a "vacation only" service). IV.

Aspects and Embodiments Specific to Consumer/Home Systems

A. Home Security—Protection Against External Attacks

1. Integration with Existing Alarm Systems

A camera system for use with the present invention may supplement a conventional alarm system by covering those aspects of a site (e.g., a house) that the conventional alarm is not configured to monitor (i.e., areas other than perimeters).

Alternatively, the system may reinforce a conventional alarm system. Because conventional security systems suffer from chronic false alarms, the system may solve this problem by providing an intermediate confirmation step before alarm signals are transmitted to responding authorities. That is, when a home alarm is tripped, the camera system may turn on so that one or more viewers can determine whether the alarm was triggered in response to a bona fide emergency.

2. "Real Time" Evacuation Plans

In a home setting, there are many threats to guard against, including fire and burglary. Because patrollers would have a detached, "birds eye" view of the entire premises, operators of the system (e.g., Net Patrol) may offer to provide "real-time" evacuation plans based on the threat. In other words, patrollers may come up with an "on the fly" evacuation plan to steer residents away from the dangerous areas (e.g., rooms on fire, rooms where the perpetrator is hiding) and send audio instructions (e.g., to speakers at the premises) on how to safely evacuate.

3. Privacy Issues

Home security system customers may also be particularly concerned about privacy issues. Accordingly, there may be an initial, randomized pre-screening by trained professionals for sensitive images before they are sent to ad hoc patrollers for viewing. Further, to deter unauthorized distribution of images, transmitted images may be watermarked or otherwise identified.

Likewise, home security system customers may be concerned about the ability of patrollers to use received images to plan a crime. Accordingly, as mentioned above, images may be transmitted randomly, based on geographical constraints, on a one-time-only basis, or the like.

B. Home Monitoring—Lifestyle Family-Oriented Systems

1. Elderly Person Monitoring Product

A related product for monitoring elderly people may aim to make sure that subjects are properly tended to (e.g., if they fall) and to make sure that subjects do not put themselves in dangerous situations (e.g., getting in the car, drinking, taking the wrong medication). However, such a product may be particularly susceptible to privacy concerns. Accordingly, images of elderly people may be digitally modified so as to conceal identity (e.g., stock photo substitution for person's body or face; replacement of person's image with outline shape or avatar). Additionally or alternatively, elderly subjects may be assured that only "qualified" professionals (i.e., nurses) are watching the camera feeds.

2. Child Monitoring Product

Similarly, a product for monitoring children would ideally serve the same purposes (safety). For example, because swimming pools can be "no man" (i.e., no child) zones at certain times (e.g., when parents are at work), the Net Patrol system may be employed to monitor the pool. Similarly, the Net Patrol system may be used to monitor and prevent consumption of alcohol (e.g., cameras located by a liquor cabinet) and chemicals (e.g., cameras located under a kitchen cabinet). Indeed, the Net Patrol system could work to make sure that teenagers or babysitters are not hosting parties at the residence (e.g., volume-based prescreening; quasi-binary decisions as discussed above).

Indeed, the Net Patrol system may be applied to quality-ensure the work of babysitters and day-care facilities. For example, patrollers may be asked to monitor "2 man zones" to confirm that at least 2 people are in the picture (i.e., that the babysitter is in the same room as the child). Likewise, patrollers may simply be asked to report whether inappropriate behavior is taking place (e.g., physical danger to the child).

Aspects and Embodiments Specific to Business Systems

There may be specific service improvements uniquely designed for businesses. For example, patrollers may be employed to watch for and report theft, thereby reducing shrinkage at retail establishments. Cameras can be set up to enable viewing of self-service check-out isles, the area underneath shopping carts, and employee backrooms. Indeed, the retailer may post a bounty to catch shoplifters.

Additional Embodiments

A. Monitoring sessions (or at least short-loop portions thereof) may be recorded and stored for later reference (e.g., when an insurance claim 1s adjudicated, to prove emergency responder activity as discussed above, etc.).

B. If the customer's monitoring devices are not engaged, the operator of the system (e.g., Net Patrol) could not reasonably be held accountable because the system would not be activated. Accordingly, the central computer may email encrypted (e.g., time stamped) codes to customers to prove when its on/off duty.

C. The system may be utilized in quasi-private property contexts (i.e., property where there are highly personal interests, but not necessarily real property ownership):

a. "Neighborhood Watch" embodiment: Cameras may be placed on neighbors' cars, on telephone poles, etc., and artificial-intelligence (AI) prescreening may be utilized to scan for apparently odd behavior, in which case feeds or images would be provided to patrollers for viewing. For example, AI could detect fire (e.g., via thermal-imaging) and where cars shouldn't be stopped/"no standing zones" (e.g., via motion detectors).

b. School embodiment: Parents of both public and private schools students may pay patrollers (e.g., indirectly through Net Patrol) to monitor areas where children frequent with minimal adult supervision or areas where children are likely to be put in dangerous situations. For example, cameras may be put on playgrounds, in school busses, at bus stops, and the like to monitor for unscrupulous individuals (e.g., kidnappers, drug dealers, etc.) or dangerous behavior (e.g., altercations, drug use, etc.).

In one embodiment, after an initial set of Net Patrollers determines that a potential security breach is underway (i.e., that there IS a person in the picture), a series of images from the site are transmitted to one or more Patrollers who view the plurality of images and vote for/select the image that is most representative/useful of the potential security breach. For example, from a plurality of images containing a suspicious person, a Net Patroller may select the images that best show the person's face. The selected images are then sent to property owners, first responders, or the like, who may determine whether or not the person is authorized to enter the premises or not. Thus, in this embodiment, a whole series of images relevant to an "incident" are reviewed by Net Patrollers, and some of which may be forwarded to property owners.

In some embodiments, images from several cameras at the monitored site are transmitted to the property owner once a potential security breach is detected. For example, cameras aimed at "approach zones" of a house (e.g., driveway, doorways) may provide images taken just before the potential security breach (i.e., such images may be temporarily stored via "short loop" in case such incident arises). In this way, property owners are provided with several incident-relevant images for evaluation.

What is claimed is:

1. A method comprising, by one or more computing systems:
    selecting one or more users registered with a content distribution network to monitor images, wherein each registered user is associated with a user profile including unique identification data and an image review accuracy score;
    receiving, at one or more servers associated with the content distribution network, one or more images to be reviewed, wherein the one or more images are associated with an escalation level;
    sending, using one or more processors associated with the one or more servers, the one or more images to at least one registered user;
    receiving, using the one or more processors, instructions from the at least one registered user; and
    executing, using the one or more processors, an action based on the received instructions.

2. The method of claim 1, wherein the received instructions comprise confirmation of a security breach.

3. The method of claim 1, wherein the received instructions comprise instructions to stand down image escalation.

4. The method of claim 1, wherein the received instructions comprise instructions to close out one or more site alerts associated with the one or more images.

5. The method of claim 1, wherein the one or more images comprise one or more buffers of images captured at one or more monitoring devices.

6. The method of claim 1, wherein the sending the one or more images to at least one registered user comprises:
    providing the one or more images in a supervisor interface.

7. The method of claim 6, wherein the received instructions comprise instructions to access real-time full motion images from one or more monitoring devices, present all captured images related to a site alert, present one or more images in full resolution, present one or more images in thumbnail format, adjust motion sensor zones for monitoring devices, adjust sensitivity for monitoring devices, adjust pan/tilt/zoom settings for one or more monitoring devices, enable two-way audio communication using one or more monitoring devices, or dispatch alert data and images.

8. The method of claim 6, wherein the supervisor interface is accessible by a SSL connection from a browser.

9. The method of claim 6, wherein the supervisor interface requires secure authentication of the at least one registered user using a hardware-based key generation device.

10. The method of claim 6, wherein the supervisor interface provides access using role-based permissions.

11. The system of claim 1, wherein the processors being operable when executing the instructions to send the one or more images to at least one registered user comprises the processors being further operable to:
    provide the one or more images in a supervisor interface.

12. The system of claim 11, wherein the received instructions comprise instructions to access real-time full motion images from one or more monitoring devices, present all captured images related to a site alert, present one or more images in full resolution, present one or more images in thumbnail format, adjust motion sensor zones for monitoring devices, adjust sensitivity for monitoring devices, adjust pan/tilt/zoom settings for one or more monitoring devices, enable two-way audio communication using one or more monitoring devices, or dispatch alert data and images.

13. The system of claim 11, wherein the supervisor interface is accessible by a SSL connection from a browser.

14. The system of claim 11, wherein the supervisor interface requires secure authentication of the at least one registered user using a hardware-based key generation device.

15. One or more computer-readable non-transitory storage media embodying software that is operable when executed to:
    select one or more users registered with a content distribution network to monitor images, wherein each registered user is associated with a user profile including unique identification data and an image review accuracy score;
    receive, at one or more servers associated with the content distribution network, one or more images to be reviewed, wherein the one or more images are associated with an escalation level;
    send, using one or more processors associated with the one or more servers, the one or more images to at least one registered user;
    receive, using the one or more processors, instructions from the at least one registered user; and
    execute, using the one or more processors, an action based on the received instructions.

16. The media of claim 15, wherein the received instructions comprise confirmation of a security breach.

17. The media of claim 15, wherein the received instructions comprise instructions to stand down image escalation.

18. The media of claim 15, wherein the received instructions comprise instructions to close out one or more site alerts associated with the one or more images.

19. The media of claim 15, wherein the one or more images comprise one or more buffers of images captured at one or more monitoring devices.

20. A system for a content distribution network, comprising:
- one or more processors associated with one or more servers; and
- a memory coupled to the processors comprising instructions executable by the processors, the processors being operable when executing the instructions to:
  - select one or more users registered with a content distribution network to monitor images, wherein each registered user is associated with a user profile including unique identification data and an image review accuracy score;
  - receive one or more images to be reviewed, wherein the one or more images are associated with an escalation level;
  - send the one or more images to at least one registered user;
  - receive instructions from the at least one registered user; and
  - execute an action based on the received instructions.

\* \* \* \* \*